(12) United States Patent
Rinehart et al.

(10) Patent No.: US 10,434,255 B2
(45) Date of Patent: Oct. 8, 2019

(54) SYSTEM AND METHOD FOR CLOSED-LOOP PATIENT-ADAPTIVE HEMODYNAMIC MANAGEMENT

(71) Applicant: The Regents of the University of California, Oakland, CA (US)

(72) Inventors: Joseph B. Rinehart, Newport Beach, CA (US); Maxime Cannesson, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 553 days.

(21) Appl. No.: 14/085,162

(22) Filed: Nov. 20, 2013

(65) Prior Publication Data

US 2014/0188072 A1  Jul. 3, 2014

Related U.S. Application Data

(62) Division of application No. 13/349,114, filed on Jan. 12, 2012, now Pat. No. 8,617,135.

(Continued)

(51) Int. Cl.
| | |
|---|---|
| *G01N 33/48* | (2006.01) |
| *A61M 5/172* | (2006.01) |
| *A61B 5/029* | (2006.01) |
| *A61M 5/142* | (2006.01) |
| *A61M 5/168* | (2006.01) |

(Continued)

(52) U.S. Cl.
CPC ........... *A61M 5/1723* (2013.01); *A61B 5/029* (2013.01); *A61B 5/4833* (2013.01); *A61M 5/142* (2013.01); *A61M 5/16877* (2013.01); *G06F 19/3468* (2013.01); *A61B 5/021* (2013.01); *A61B 5/0245* (2013.01); *A61B 5/0295* (2013.01); *A61B 5/14542* (2013.01); *A61B 5/7203* (2013.01); *A61M 2202/0208* (2013.01); *A61M 2205/502* (2013.01); *A61M 2205/52* (2013.01); *A61M 2230/00* (2013.01); *A61M 2230/04* (2013.01)

(58) Field of Classification Search
None
See application file for complete search history.

(56) References Cited

U.S. PATENT DOCUMENTS

| | | |
|---|---|---|
| 4,308,866 A | 1/1982 | Jelliffe et al. |
| 5,573,007 A | 11/1996 | Bobo, Sr. |

(Continued)

FOREIGN PATENT DOCUMENTS

JP   2005326943   11/2005

OTHER PUBLICATIONS

Office Action dated Nov. 6, 2013 issued in connection with related U.S. Appl. No. 13/349,058.

(Continued)

*Primary Examiner* — Larry D Riggs, II
(74) *Attorney, Agent, or Firm* — Brooks Kushman P.C.

(57) ABSTRACT

A system and method for patient-adaptive hemodynamic management is described. One embodiment includes a system for hemodynamic management including transfusion, volume resuscitation with intravenous fluids, and medications, utilizing monitored hemodynamic parameters including the described dynamic predictors of fluid responsiveness, and including an intelligent algorithm capable of adaptation of the function of the device to specific patients.

5 Claims, 28 Drawing Sheets

Related U.S. Application Data

(60) Provisional application No. 61/432,081, filed on Jan. 12, 2011.

(51) Int. Cl.
*A61B 5/00* (2006.01)
*G06F 19/00* (2018.01)
*A61B 5/021* (2006.01)
*A61B 5/0245* (2006.01)
*A61B 5/145* (2006.01)
*A61B 5/0295* (2006.01)

(56) References Cited

U.S. PATENT DOCUMENTS

| | | | |
|---|---|---|---|
| 5,677,290 | A | 10/1997 | Fukunaga |
| 5,957,885 | A | 9/1999 | Bollish et al. |
| 5,984,893 | A | 11/1999 | Ward |
| 6,305,373 | B1 | 10/2001 | Wallace et al. |
| 6,776,764 | B2 | 8/2004 | Pinsky |
| 6,807,965 | B1 | 10/2004 | Hickle |
| 7,229,430 | B2 | 6/2007 | Hickle et al. |
| 9,022,974 | B2 | 5/2015 | Rinehart et al. |
| 2003/0167010 | A1* | 9/2003 | Pinsky ............... A61B 5/02007 600/485 |
| 2005/0010166 | A1 | 1/2005 | Hickle |
| 2007/0213658 | A1 | 9/2007 | Hickle |
| 2008/0183060 | A1* | 7/2008 | Steil .................. A61B 5/14865 600/365 |
| 2008/0194924 | A1 | 8/2008 | Valk et al. |
| 2008/0201325 | A1 | 8/2008 | Doniger et al. |
| 2008/0228133 | A1* | 9/2008 | Hildebrand ........... A61M 5/142 604/66 |
| 2009/0076462 | A1 | 3/2009 | Kiani |
| 2009/0326510 | A1 | 12/2009 | Haefner et al. |
| 2010/0081942 | A1 | 4/2010 | Huiku |
| 2010/0204557 | A1 | 8/2010 | Kiaie et al. |
| 2010/0249559 | A1 | 9/2010 | Lovejoy |
| 2010/0268157 | A1* | 10/2010 | Wehba ................ G06F 19/3468 604/66 |
| 2010/0273738 | A1 | 10/2010 | Valcke et al. |
| 2010/0298765 | A1 | 11/2010 | Budiman et al. |
| 2011/0112442 | A1 | 5/2011 | Merger et al. |
| 2011/0270047 | A1 | 11/2011 | O'Brien |
| 2012/0179007 | A1 | 7/2012 | Rinehart et al. |
| 2012/0179136 | A1 | 7/2012 | Rinehart et al. |
| 2014/0081201 | A1 | 3/2014 | Rinehart et al. |
| 2015/0209514 | A1 | 7/2015 | Rinehart et al. |

OTHER PUBLICATIONS

Jun. 16, 2016 Office Action in related U.S. Appl. No. 13/349,168.
Jan. 29, 2016 Office Action in related U.S. Appl. No. 13/349,168.
Jun. 1, 2015 Office Action in related U.S. Appl. No. 13/349,168.
Jul. 21, 2014 Office Action in related U.S. Appl. No. 13/349,168.
Mar. 15, 2016 Office Action in related U.S. Appl. No. 14/085,138.
Oct. 22, 2015 Office Action in related U.S. Appl. No. 14/085,138.
Jun. 10, 2015 Office Action in related U.S. Appl. No. 14/085,138.
Feb. 16, 2016 Office Action in related U.S. Appl. No. 13/349,012.
Oct. 23, 2015 Office Action in related U.S. Appl. No. 13/349,012.
Mar. 30, 2015 Office Action in related U.S. Appl. No. 13/349,012.
Sep. 26, 2014 Office Action in related U.S. Appl. No. 13/349,012.
Jose Ot Avio Auler et al: "Online Monitoring of Pulse Pressure Variation to Guide Fluid Therapy After Cardiac Surgery", Anesthesia and Analgesia.,vol. 106 (2008), pp. 1201-1206.
M. Biais et al: "Uncalibrated pulse contour-derived stroke volume variation predicts fluid responsiveness in mechanically ventilated patients undergoing liver transplantation", British Journal of Anaesthesia., vol. 101 (2008), pp. 761-768.
Nov. 6, 2013 Office Action in related U.S. Appl. No. 13/349,058.
Oct. 23, 2017 Office Action in related U.S. Appl. No. 14/680,706.
Oct. 17, 2016 Office Action in related U.S. Appl. No. 14/085,138.
Sep. 16, 2016 Office Action in related U.S. Appl. No. 13/349,012.
Rinehart, J., et al., Closed-loop systems in anesthesia: Is there a potential for closed-loop fluid management and hemodynamic optimization?, Anesth. Analq. (2012) 114(1):130-43; Epub Sep. 29, 2011.
Rinehart, J., et al., Evaluation of a novel closed-loop fluid-administration system based on dynamic predictors of fluid responsiveness: an in silico simulation study, Crit Care (2011) 15(6):R278. Epub Nov. 23, 2011.

* cited by examiner

Table 1: Fluid Management: Practitioners vs. Closed-Loop

| Group | (1) Anesthesiologist Managed | (2) Anesthesiologist Managed Pressors, Closed-loop Fluids | (3) Closed-loop Managed | (4) No Management |
|---|---|---|---|---|
| First Bolus (minutes) | 21.5 ±5.6* | 15.6 ±1.1 | 16.0 ±1.3 | - |
| Total Fluid Given (ml) | 1968 ±644* | 2875 ±275 | 2675 ±244 | - |
| Mean Arterial Pressure (mmHg) | 76 ±4.2 | 79 ±2.0 | 79 ±1.1 | 61 ±6.9 |
| Mean Cardiac Output During Case (L/min) | 5.2 ±0.6* | 5.8 ±0.2** | 5.9 ±0.2** | 3.8 ±0.4 |
| Final Cardiac Output (L/min) | 4.8 ±1.5* | 5.6 ±0.5** | 5.7 ±0.4** | 1.7 ±0.9 |
| Cardiac Output During Case, Coefficient of Variation (%) | 36.7 ±23* | 16.6 ±9** | 16.3 ±8** | 89 ±29 |

Data are reported as mean +/- standard deviation. * $p<0.05$ vs. groups 2, 3, and 4. ** $p<0.05$ vs. groups 1 & 4.

FIG. 27

SYSTEM AND METHOD FOR CLOSED-LOOP PATIENT-ADAPTIVE HEMODYNAMIC MANAGEMENT

CROSS-REFERENCE TO RELATED APPLICATIONS

The present application claims the benefit of U.S. Provisional Application Ser. No. 61/432,081, filed on Jan. 12, 2011, entitled "INTELLIGENT CLOSED-LOOP, PATIENT-ADAPTIVE HEMODYNAMIC MANAGEMENT SYSTEM," which is incorporated herein by reference. This application is related to U.S. patent application Ser. No. 13/349,168 filed Jan. 12, 2012, entitled "SYSTEM AND METHOD FOR CLOSED-LOOP PATIENT-ADAPTIVE HEMODYNAMIC MANAGEMENT", to U.S. patent application Ser. No. 13/349,058 filed Jan. 12, 2012, entitled "SYSTEM AND METHOD FOR CLOSED-LOOP PATIENT-ADAPTIVE HEMODYNAMIC MANAGEMENT", and to U.S. patent application Ser. No. 13/349,012, filed Jan. 12, 2012, entitled "SYSTEM AND METHOD FOR CLOSED-LOOP PATIENT-ADAPTIVE HEMODYNAMIC MANAGEMENT". The contents of each of these applications are hereby incorporated by reference herein in their entirety for all purposes. The present application is a divisional application of U.S. patent application Ser. No. 13/349,114, filed on Jan. 12, 2012, which is incorporated by reference herein.

FIELD

The disclosure relates to an apparatus and method for hemodynamic management capable of facilitating fluid administration, transfusion of blood products, and administration of blood pressure supporting medications.

BACKGROUND

In the past, fluid resuscitation has been approached directly by clinicians using vital signs, or clinical guidelines regarding urine output, for example. Previous automated systems have been tried using either urine output or other physiologic parameters like blood pressure or heart rate, all of which have been unable to accurately predict fluid responsiveness. In some cases trial-and-error was the best option available.

Although present devices are functional, they are not sufficiently accurate or otherwise satisfactory.

SUMMARY

In one aspect the disclosure describes a method that incorporates the dynamic predictors of fluid responsiveness ("fluid predictors" i.e. pulse-pressure variation or PPV, stroke volume variation or SVV, parameters derived from the plethysmograph waveform, etc) which have been shown to reliably predict a response to fluid bolus in specific conditions. This allows directed fluid management with the goal of optimizing cardiac output.

In another aspect, a method is provided that incorporates the dynamic predictors of fluid ("fluid predictors") responsiveness in conjunction with a patient-adaptive monitoring system that adjusts output based on previous responses represents a substantial improvement over previously proposed automated systems.

Using a combination of the change in the fluid predictive parameters and the change in cardiac output in response to a bolus allows a very specific measurement of the bias present in a particular patient at a particular time and allows for patient-adaptive responses to be effected. Additionally, using a variety of available vital signs and cardiac output information allows for appropriate administration of blood-pressure supporting pharmacologic agents.

In another aspect, a method and system is provided comprising a set of processes and a device based on those used to administer IV fluids, blood and medications to patients autonomously.

In another aspect, a computer-implemented method for controlling fluid administration is provided. The method includes receiving input information relating to one or more physiologic processes of a patient, determining, based at least in part upon the input information, a subgroup of bolus log entries associated with a current state of the patient, and adjusting, using a processor, administration of fluid to the patient based at least in part upon log data included within the subgroup of bolus log entries.

In yet another aspect, a device is provided that includes one or more processors; and a memory operatively coupled to the one or more processors. The memory stores signals which, when executed by the one or more processors, cause the one or more processors to receive input information relating to one or more physiologic processes of the patient, and to determine, based at least in part upon the input information, a subgroup of bolus log entries associated with a current state of the patient. The signals further cause the one or more processors to adjust administration of fluid to the patient based at least in part upon log data included within the subgroup of bolus log entries.

In a further aspect, an infusion system includes a pump apparatus configured to control delivery of fluid to a patient, and a controller that receives input information relating to one or more physiologic processes of the patient. The controller then determines a subgroup of bolus log entries associated with a current state of the patient based at least in part upon the input information, and adjusts administration of fluid to the patient based at least in part upon log data included within the subgroup of bolus log entries.

In still another aspect, a computer-implemented method for facilitating the administration of fluid to a patient is provided. The computer-implemented method includes determining a first effect on a physiologic parameter of the patient associated with administration of a first fluid bolus to the patient, and then storing, using a processor, first information relating to the first effect in a first bolus log entry. The method further includes determining a second effect on the physiologic parameter of the patient associated with administration of a second fluid bolus to the patient, and then storing, using a processor, second information relating to the second effect in a second bolus log entry. The method further includes generating, using the processor, a fluid administration signal based at least in part upon at least one of the first bolus log entry and the second bolus log entry.

In another aspect, a device is provided that includes one or more processors, and a memory operatively coupled to the one or more processors, the memory storing program code which, when executed by the one or more processors, determines a first effect on a physiologic parameter of the patient associated with administration of a first fluid bolus to the patient, and then stores first information relating to the first effect in a first bolus log entry within device storage. The memory further stores program code which determines a second effect on the physiologic parameter of the patient associated with administration of a second fluid bolus to the patient, stores second information relating to the second effect in a second bolus log entry within the device storage, and generates a fluid administration signal based upon at least one of the first bolus log entry and the second bolus log entry.

In yet another aspect, an infusion system includes a pump apparatus configured to control delivery of fluid to a patient, and a controller. The controller of this aspect determines a first effect on a physiologic parameter of the patient associated with administration of a first fluid bolus to the patient, and stores first information relating to the first effect in a first bolus log entry within device storage. The controller then determines a second effect on the physiologic parameter of the patient associated with administration of a second fluid bolus to the patient, and stores second information relating to the second effect in a second bolus log entry within the device storage. The controller provides a fluid administration signal to the pump apparatus based upon at least one of the first bolus log entry and the second bolus log entry.

In still another aspect, a computer-implemented method for providing clinical decision support relating to the administration of fluid to a patient is provided. The method includes receiving input information relating to one or more physiologic processes of a patient, determining, based at least in part upon the input information, a subgroup of bolus log entries associated with a current state of the patient, and providing, using the processor, a fluid administration recommendation based at least in part upon log data included within the subgroup of bolus log entries.

In a further aspect, a computer-implemented method for providing clinical decision support relating to the administration of fluid to a patient is provided. The method of this aspect includes determining a first effect on a physiologic parameter of the patient associated with administration of a first fluid bolus to the patient, storing, using a processor, first information relating to the first effect in a first bolus log entry, determining a second effect on the physiologic parameter of the patient associated with administration of a second fluid bolus to the patient, storing, using a processor, second information relating to the second effect in a second bolus log entry, and providing, using the processor, a fluid administration recommendation based at least in part upon at least one of the first bolus log entry and the second bolus log entry.

In yet another aspect, a computer-implemented method for providing clinical decision support relating to the administration of fluid to a patient is provided. The method of this aspect includes receiving bolus log information relating to one or more effects on a state of the patient associated with prior administration of fluid to the patient, then determining, using a processor and based upon the bolus log information, a predicted change in a physiologic parameter of the patient in response to the administration of a fluid bolus to the patient. The method further includes providing, using the processor, a fluid administration recommendation based upon the predicted change.

In another aspect, a computer-implemented method for facilitating the administration of fluid to a patient is provided. The method of this aspect includes receiving bolus log information relating to one or more effects on a state of the patient associated with prior administration of fluid to the patient, and determining, using a processor and based upon the bolus log information, a predicted change in a physiologic parameter of the patient in response to the administration of a fluid bolus to the patient. The method further includes generating, using the processor, a fluid administration signal based upon the predicted change.

In a further aspect, a system is provided that includes: 1) a means of calculating the expected increase in cardiac output in the general population in response to a fluid bolus given a specific set of physiologic parameters. This calculation is based on previously published and unpublished data; 2) a means of calculating the expected increase in cardiac output in a specific patient given a specific set of physiologic parameters and data collected from previous fluid administrations; 3) a means of calculating bias, artifact, and error in the response to fluid, in part based on the difference between the change in actual cardiac output and the change in the dynamic predictor and the predictable relationship between the two; 4) calculations for determining whether or not blood pressure supporting medications are indicated, and if so how much; and 5) calculations for determining whether or not blood product administration is indicated, and if so how much.

In yet a further aspect, a clinical device is provided that is capable of administering fluids, blood products, and medications based on the algorithms above, monitoring the patient response, and displaying the monitored information in a specific and novel way to the practitioner. One purpose of this device is to automate and standardize administration of intravenous fluids, blood products, and blood-pressure supporting medications to assist clinicians with the eventual goal of improving outcomes.

In an additional aspect, an apparatus for hemodynamic and cardiac output management in a patient is provided, comprising a computer readable storage medium storing instructions to perform a method of managing hemodynamic and cardiac output in a patient, the method comprising the steps of determining, given a set of available physiologic data obtained from patient monitoring devices, which parameters to use and in what combinations to predict fluid responsiveness; and determining the expected increase in cardiac output in the general population in response to a fluid bolus of specific size given the chosen set of physiologic parameters; and determining patient-specific bias in the response to said fluid based on the patient's prior responses to fluid administration.

The apparatus may further comprise detecting and filtering artifact in the monitored data; and detecting and filtering error in the patient bias using the strong relationship between the predictive parameters and their response to fluid administration, especially to detect ongoing bleeding or fluid shifts which might influence bias.

The apparatus may also comprise dynamically adapting to specific patients using the known biases in conjunction with associated physiologic parameters, their means and standard deviations in relationship to one another, and observed responses to previous interventions by the apparatus; determining whether blood-pressure supporting medications are indicated and if so administer them, again monitoring responses and adapting to the patient, and determining whether blood product administration is indicated and if so administer them.

The apparatus may be further configured such that adaptation and learning is further enhanced by data shared between devices over time to improve population expectations and the processes of the apparatus.

The apparatus may be further configured such that the adapting process is concerned not only with adjustments to the fluid administration volume and threshold and to the medication administration dose and threshold, but also with automatic adjustments to the weight of each measured parameter in decision-making by the apparatus.

The apparatus may further comprise pumps capable of injecting fluid or medication into said patient.

The apparatus may be further configured to operate, in real time and without operator interaction, to automatically adjust the anticipated response to a new bolus based on the bias information in a state-dependent fashion.

In yet another aspect, a method for hemodynamic and cardiac output management in a patient is provided comprising: obtaining physiologic data from a patient, injecting fluid, medications, or blood products into a patient as indicated, measuring the results of said interventions in said patient, adapting future interventions based on data collected from previous interventions said fluid to said patient.

Those skilled in the art can readily recognize that numerous variations and substitutions may be made in the invention, its use and its configuration to achieve substantially the same results as achieved by the embodiments described herein. Accordingly, there is no intention to limit the invention to the disclosed exemplary forms. Many variations, modifications and alternative constructions fall within the scope and spirit of the disclosed invention as expressed in the claims.

As previously stated, the above-described embodiments and implementations are for illustration purposes only. Numerous other embodiments, implementations, and details of the invention are easily recognized by those of skill in the art from the following descriptions and claims.

BRIEF DESCRIPTION OF THE DRAWINGS

Various objects and advantages and a more complete understanding of the present invention are apparent and more readily appreciated by reference to the following Detailed Description and to the appended claims when taken in conjunction with the accompanying Drawings wherein:

FIG. 27 is a summary of results from initial studies using the methodology of the control device in simulations.

Figure 1A:
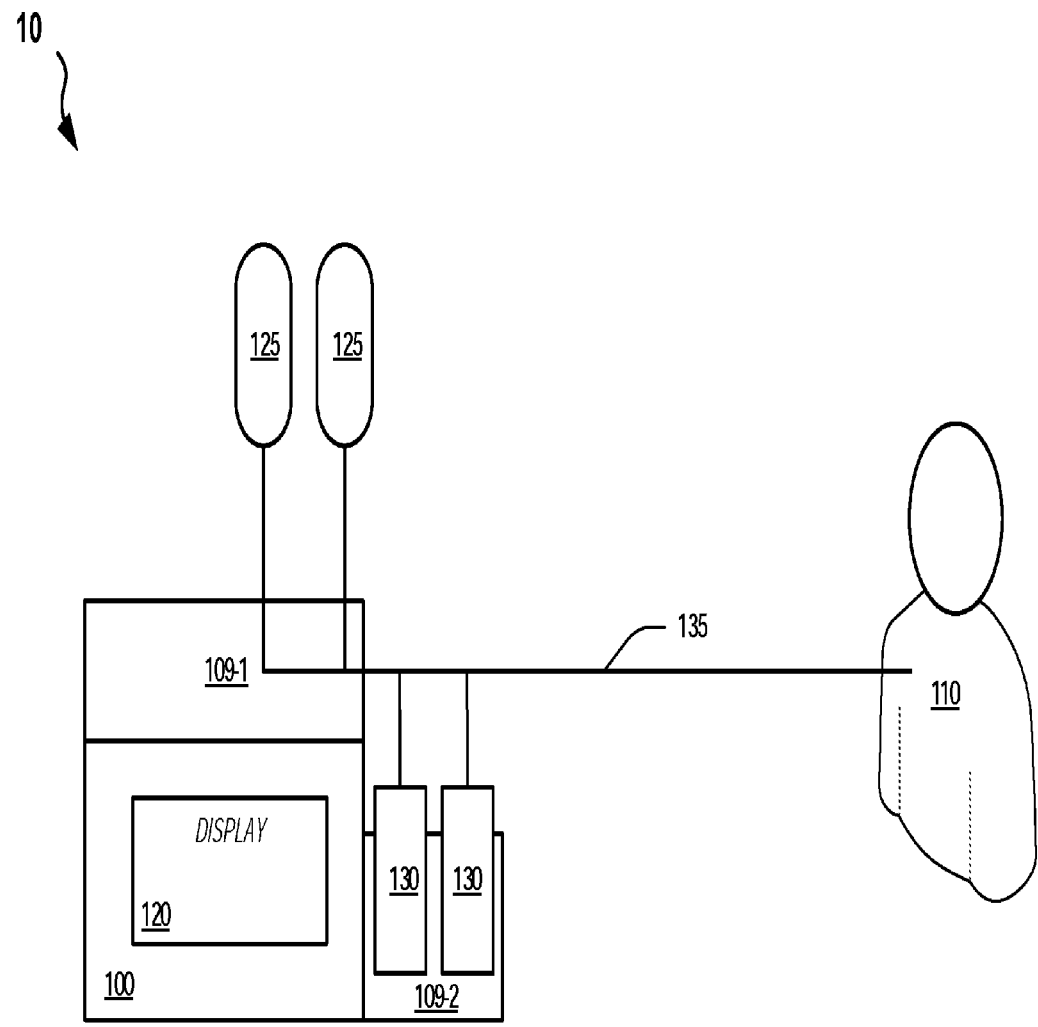
FIG. 1A illustrates details of an exemplary patient-adaptive hemodynamic management system in accordance with the disclosure.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

An intelligent, closed-loop, patient-adaptive hemodynamic management system and method are provided to monitor hemodynamic parameters, including those predictive of fluid responsiveness, the system being capable of fluid administration, transfusion of blood products, and administration of blood pressure supporting medications based on those parameters in conjunction with patient-adaptive algorithms as well as pooled patient data, and displaying the monitored parameters in a way easily interpreted by practitioners.

The system and method provided are based on hemodynamic monitoring including dynamic parameters of fluid responsiveness ('fluid predictors') derived from arterial pressure waveform, plethysmograph wave form, thoracic ultrasound, bioimpedance, bioreactance or EKG waveform, for example.

This control device and process are designed to utilize, among other physiologic data, the dynamic predictors of fluid responsiveness ('fluid predictors'). As there are several described parameters that meet these criteria such as, for example, pulse-pressure variation (PPV), stroke volume variation (SVV), plethysmograph variability, and EKG waveform characteristics, the description will simply refer to the group as the "Fluid Predictors" or FP. This term should be taken to mean any of the described predictors of fluid responsiveness.

Additionally, all of the physical values and constants in the disclosure are subject to change based on results of ongoing studies as the device and algorithm are refined; values contained herein should be taken to be exemplary at the time of this writing.

Other terms and abbreviations used herein include:

CO-Cardiac output

Patient or Subject—the "patient" or "subject" is the organism being monitored by and managed by the system. In one embodiment, the patient is a human being. In another embodiment, the patient may be any mammal, reptile, amphibian, or bird of sufficient size to make intravascular resuscitation an appropriate strategy for management of cardiac output and oxygen delivery.

Vital Signs or Vitals—Any statistical measure of a physiologic process taking place in a patient—including waveforms derived from physiologic processes. Vitals can include, for example:

Heart Rate (HR)—the number of ventricular contractions per minute

Stroke Volume (SV)—the volume of blood ejected by the left ventricle during contraction in milliliters.

Systolic Blood Pressure (SBP)—the highest blood pressure felt in the systemic arterial vascular tree during a cardiac cycle.

Diastolic Blood Pressure (DBP)—the lowest blood pressure felt in the systemic arterial vascular tree during a cardiac cycle.

Mean Arterial Pressure (MAP)—the average blood pressure in the systemic arterial system over one or more cardiac cycles, typically calculated as ((SBP+DBP+DBP)/3).

Systemic Vascular Resistance (SVR)—An index of arteriolar constriction throughout the body measured in dyn·s/cm−5

Cardiac Output—the total volume of blood ejected by the left ventricle over one minute Dynamic Predictor (DP)—one or more measures of preload dependence derived from the arterial pressure waveform, plethysmograph waveform, EKG waveform, thoracic ultrasound, bioimpedance, bioreactance, and including specific maneuvers such as passive leg raising and tele-expiratory pause. As there are several described parameters that meet this criteria (pulse-pressure variation, stroke volume variation, plethysmograph variability, EKG waveform variation in lead II, and more) the phrase Dynamic Predictor will be understood to represent any one or more of the measures in this group. The term fluid predictor may be used interchangeably with the term Dynamic Predictor in the present disclosure.

Intravenous fluid (IV Fluid)—any fluid intended for administration intravenously to a monitored subject for the purpose of intravascular volume expansion or increasing oxygen delivery. IV Fluid would therefore include, but not be limited to: crystalloid solutions like Lactated Ringer's Solution, Normal Saline, Dextrose Solutions, Plasmalyte, and in general balanced salt solutions and sugar solutions; colloidal solutions like albumins, starches, and similar; and blood products and blood analogs like whole blood, platelets, fresh frozen plasma, cryoprecipitate, packed red blood cells, salvaged cellular solutions, or any substitutes meant to mimic or replace these products.

Fluid bolus—an administration of a specific volume of IV Fluid over a discrete timespan.

Supervisor (system supervisor, user)—a human user who monitors system operation, and who may, in one embodiment, accept or reject system recommendations before the system acts on those recommendations, and who may, in another embodiment, at any time, override system operation in favor of a user directed action.

"Efficacy" of a Fluid Bolus—the degree to which the intravascular administration of said fluid increases the cardiac output; or the degree to which the intravascular administration of said fluid improves the delivery of oxygen to the tissues, for example.

Prediction—the calculated percent increase in cardiac output that a fluid bolus would be expected to cause in the patient.

Vasoactive Medications—medications controlled by the system that could include those intended to manipulate blood pressure and cardiac output such as, for example, ephedrine, phenylephrine, norepinephrine, epinephrine (adrenaline), dopamine dobutamine, milrinone, dopexamine, nitroglycerine, nitroprusside, and other vasopressors, inotropes, and vasodilators.

With reference to FIG. 1A, a patient-adaptive hemodynamic management system 10 includes a control device 100 coupled via electronic interfaces (not shown) to a first fluid pump 109-1 and a second fluid pump 109-2. The control device 100 includes a display 120. The display 120 includes a display screen, electronics and interfaces coupled to the first and second fluid pumps 109-1 and 109-2. The first fluid pump 109-1 is coupled to fluid sources such as, for example, IV bags 125 containing any of various IV fluids. The second fluid pump 109-2 is coupled to medications such as, for example, medication vials 130 containing fluid medications. The IV bags 125 and medication vials 130 are fluidically coupled to IV tubing 135 which is coupled to a patient 110 such that the IV fluids and medication can be administered to the patient and dynamically controlled by the control device 100.

The control device 100 includes one or more processing units (not shown), and one or more computer readable storage medium (not shown). The processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof. The computer readable storage medium may include one or more memories for storing data, including read only memory (ROM), random access memory (RAM), magnetic RAM, core memory, magnetic disk storage mediums, optical storage mediums, flash memory devices and/or other machine readable mediums for storing information. The computer readable storage medium may be embodied in one or more portable or fixed storage devices, optical storage devices, wireless channels, and/or various other storage mediums capable of storing that contain or carry instruction(s) and/or data.

The control device 100 is coupled to the fluid pumps 109 via interface ports. The interface ports can include one or more of a standard USB port and a standard serial port. The USB connector can also be used to import patient data in real-time from another source such as a patient monitor (not shown). Optionally, an external component may be connected to the control device 100 which will allow for direct monitoring of patient vital signs by the control device 100. Finally, the USB/Serial ports will allow data to be transferred to and from the control device 100 for sharing data with other networked equipment (not shown), and for receiving firmware upgrades. Additional ports may be added (for interface with electronic records systems, for example).

In some embodiments, the display 120 provides a touch-screen interface for monitoring vital signs of the patient and for entering patient data and user preferences into the control device 100.

The first fluid pump 109-1 can be integrated in the same housing as the control device 100 or can be an external pump. In either case, the first fluid pump 109-1 can regulate and drive the flow of fluid from the IV bags 125 to the patient, as well as select which fluid to use from which IV bag 125. The IV fluids can include one or more of crystalloids, colloids, or blood products as well as other fluids. The second fluid pumps 109-2 can be integrated with or external to the control device 100 and can be syringe pump systems for use with multiple medication vials 130. One or more pumps may be included but are not required for standard use. The fluid pumps 109 can also contain an air detector to hold the infusion in the event air is detected in the tubing. The control device 100 can be coupled to commercially available pumps to control those.

The IV tubing 135 is typically disposable and is coupled with the control device after flushing and prior to use, as for any standard IV fluid pump. The IV tubing 135 is depicted as a single tube at the patient 110 and multiple tubes at the IV bags 25 and the medication vials 130. However, multiple IV tubes 135 can be connected to the patient 110. The disposable IV tubing 135 is sterile IV tubing where a new disposable tube set is used for each patient to maintain sterility. One end of IV tubing 135 can have standard IV bag taps for use with standard IV solutions, colloids, and blood products. The opposite end of the IV tubing 135 can be a male luer lock for connection to standard IV tubing sets and claves. The disposable IV tubing can also have side ports distal to the main fluid pump which the medication syringes from the medication vials 130 can be attached to.

Figure 1B:
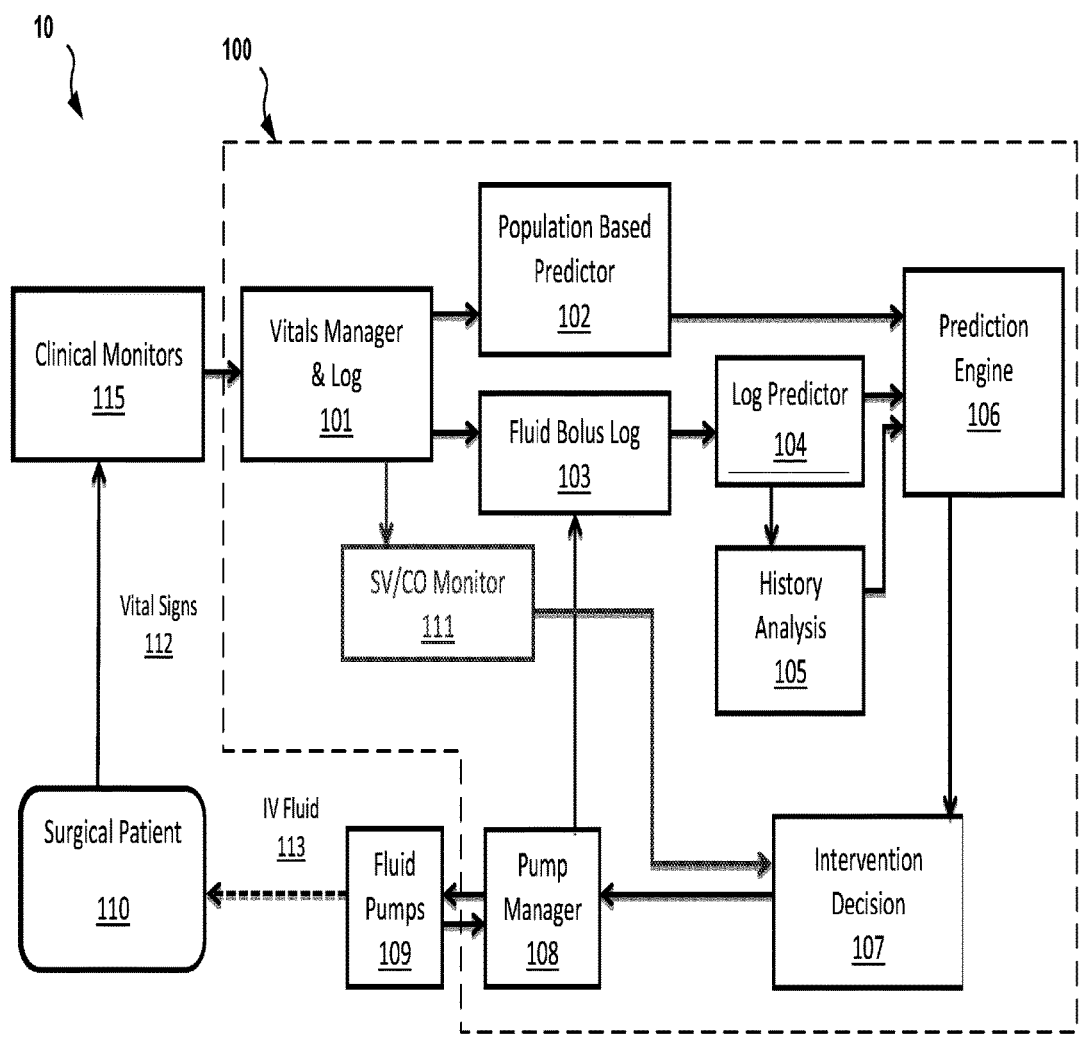
FIG. 1B illustrates details of an embodiment of a control device that can be used, for example, in the system of FIG. 1A.

FIG. 1B illustrates the system 10 including details of an embodiment of the control device 100. Each of the components of the control device 100 shown in FIG. 1B are described in detail in the figures and sections that follow.

Referring to FIG. 1B, the surgical patient 110 is monitored by one or more clinical monitors 115, which are coupled with the control device 100. The clinical monitors 115 can be integrated with or separate from the control device 100. The vitals measured by the clinical monitors 115 are communicated in some fashion to a vitals manager and log component 101, which, in some embodiments, filters the incoming data for noise and validity and then maintains an ongoing record of the validated data in a vitals log.

Data from the vitals manager component 101 is passed on request to the population based predictor component 102. The population based predictor component 102 is responsible for making predictions about the likely efficacy of a certain fluid bolus by comparing the received vitals of the patient 110 to mean responses obtained from a previous population of patients with similar vitals in response to the certain fluid bolus.

Data from the vitals manager component 101 is also passed, on request in some embodiments, to a fluid bolus log component 103. The data is typically passed or requested when a fluid bolus is initiated or terminated, so that the vitals and calculations based on them may be included in the fluid bolus log with the appropriate bolus. The fluid bolus log component 103 also receives inputs from a pump manager component 108 (e.g., when fluid boluses are initiated or terminated) including the relevant details of the bolus being administered.

Information from the fluid bolus log component 103 is output to a log predictor component 104. The log predictor component 104 is configured to analyze the known history of the current patient 110, and, taking into account the vitals and sub-analyses based on the vitals, predict the current efficacy of a fluid bolus.

The log predictor component 104 is also configured, after determining the appropriate segments of the Log that are applicable to the patient 110 in the current state and finishing its predictive analysis, to pass the same segments it used for analysis on to a history analysis component 105. The history analysis component 105 then further characterizes these segments to examine the mean historical error of both the population based predictor component 102 and the log predictor component 104 by determining, for example, the standard deviation of these errors in order to make corrections to current predictions.

A prediction engine 106 takes the outputs from the population based predictor component 102, the log predictor component 104, and the history analysis component 105, and uses these outputs to formulate a combined prediction in cardiac output for the current state of the patient 110. This combined prediction is passed on to an intervention decision component 107 which takes the predicted change in cardiac output and determines the appropriate course of action for the control device 100. This action may be modified by user specifications in this component.

Finally, the action dictated by the intervention decision component 107 is communicated to the pump manager component 108, which is responsible for communication of the action with a supervisor for verification (if necessary) and the actual hardware level control and monitoring of the fluid pump(s) 109.

The fluid pump(s) 109, in one embodiment, are externally controlled fluid pumps which contain their own command interface, alarm system, and configuration. The control of the fluid pumps 109 can be achieved over serial, network, wireless, Bluetooth, or other electronic protocols. The specific design of the fluid pumps 109 is not essential beyond the characteristic that they are able to variably control the rate of administration of IV Fluid and/or medication 113 into the patient 110. There may be one, two, or more than two physical fluid pumps 109, depending on the embodiment.

In another embodiment, the fluid pump(s) 109 are an integrated component of the control device 100. In this embodiment, the fluid pumps 109 may or may not include alarm and control configurations. If the fluid pumps 109 do not include alarms and controls, the alarms and controls for the pumps can be included in the control device 100. A user interface (not shown) of the control device 100 can be used to affect some aspects of the fluid pumps 109. There may be one, two, or more physical pumps 109 in this embodiment.

In yet another embodiment, the fluid pump(s) 109 are the embodiment of a control device 100 with the entirety of the system built into the hardware and electronic control scheme of the fluid pump 109. This pump may include one, two, or more individual fluid set channels for control.

As expected, the fluid pump(s) 109, deliver IV fluid and/or medications 113 to the patient 110 at the rate and times dictated by the method of the claim, in some cases as approved by the supervisor.

An SV/CO monitor 111 is another component that keeps track of the stroke volume and cardiac output over time. The SV/CO monitor 111 can independently provide information about the current stroke volume and cardiac output compared to the average and maximum SV/CO and this information can be used by the intervention decision component 107 either alone or in conjunction with the other components to determine whether or not to provide fluid to the patient.

Figure 2:
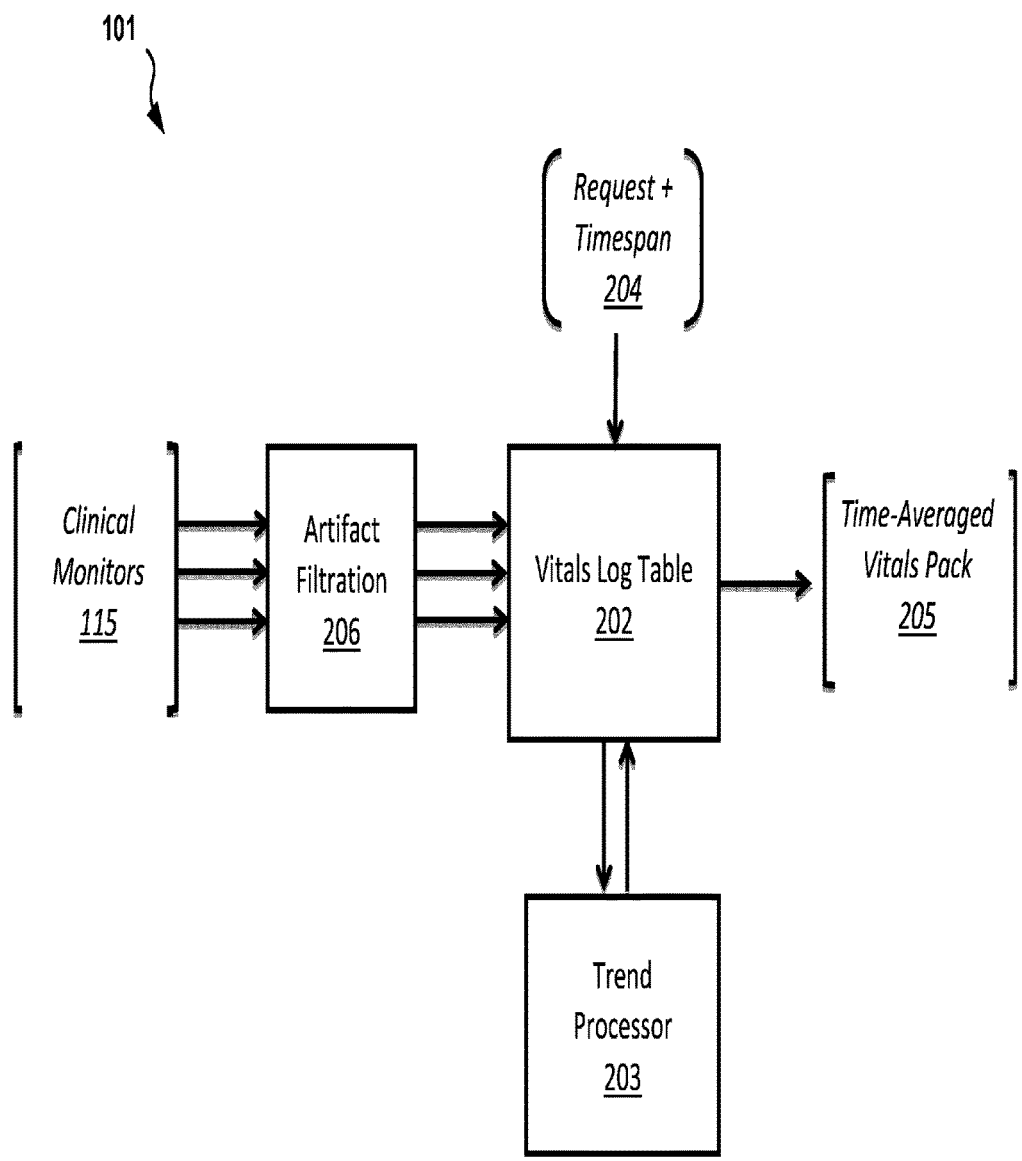
FIG. 2 illustrates details of an embodiment of a vitals manager and log component that can be used, for example, in the control device of FIG. 1B.

FIG. 2 illustrates details of an embodiment of a vitals manager component 101 that can be used, for example, in the management system 10 of FIGS. 1A and 1B. The vitals manager component 101 is responsible for the acceptance and processing of new vital signs received from clinical monitors 201. In one embodiment, clinical monitors 115 are included within the control device 100 and are connected to the patient 110 and simply pass the collected data along to the vitals manager component 101 internally. In another embodiment, external or third-party clinical monitors 115 are connected to the patient and the data from the clinical monitors 115 is sent to the control device 100 through data interfaces using communications protocols, including but not limited to direct serial connections/RS232, TCP/IP or other network protocols including wireless and Bluetooth, USB, and direct analog signals. This data, in a one embodiment, could be expected to arrive about every second, but may be as often as every ¹⁄₁₀₀₀th of a second or less in the case of digitized waveforms or even continuously in analog signals, and may be as infrequent as once a minute in low-performance embodiments.

Regardless of the original source of the information, the vital signs data 112 is received by the vitals manager component 101 and first pass through an artifact and noise filter component 206, referred to from herein as the artifact filtration component 206. The artifact filtration component 206 compares the new vital signs data 112 both to itself (for internal consistency) and to previously received data (for consistency with regards to trends and time), and to general rules about limits on specific parameters. If the new vital signs data 112 is found to satisfy the requirements of the noise filters (e.g., within threshold limits and/or within threshold changes over a threshold time) it is deemed valid and passed on to the Vitals Log table 202. If not, it is rejected as being a temporary artifact and the vital signs data 112 discarded.

To accomplish this artifact detection, in one embodiment, a mean value and standard deviation can be calculated for any parameter in relationship to any other hemodynamic parameter over time. This calculation is performed for any relevant decision-making variables (for example, the DP and CO). If the target parameter is outside the standard deviation for the associated parameters of comparison, it is more likely that this new measurement is an artifact and will be flagged by the system and temporarily ignored.

Over the next few measurements, if the target variable returns to a range expected for the associated variables, the previously detected artifact value(s) is/are left flagged and are ignored in any analysis or processing of the vital signs data 112. However, if the target variable remains outside the expected range for longer than a discrete timespan, or the incoming vital signs data 112 change such that they are now in ranges correlating with the vital sign of interest, the flags are removed and the measurement is assumed to be real.

Additionally, certain parameters measured from the same equipment/monitors will be expected to reflect artifacts simultaneously. For example, a heart rate, blood pressure, and stroke volume variation from an arterial line waveform would be expected to either all show artifact or none if the signal were to become noisy.

Similarly, a parameter monitored from different clinical monitors 115 but reporting the same vital sign (for example, a heart rate calculated from the EKG waveform, arterial line waveform, and plethysmograph waveform) would be expected to change in all three measurements. If there is a significant difference between measurements from different clinical monitors 115, the artifact filtration component 206 can determine that there is artifact in one or more of the signals and that one or more of the measurements is likely incorrect.

Referring again to FIG. 2, a Vitals Log table 202, in one embodiment, maintains a complete record of all vital signs data 112 accepted from the clinical monitors 115 regarding the patient 110, whether temporally contiguous or not. Further, should a different control device 100 be used on the same patient 110, the data from a previous control device 100 could be transferred to the new vitals log table 202 of the new control device 100, either over a network, through a portable media device like a USB drive or electronic smart card, or via some other form of electronic media. At any time, the vitals log table 202 will service vitals request inputs 204 for patient data at given times that are received, for example, from other components of the management system 10. Said vitals request inputs 204 can include both a time point and a time span (e.g., a start time and an end time, or a start time and duration). The time span indicates the period over which the vitals log table 202 should compile and average (or perform other statistical analysis on) the requested data. The time point indicates when this average time frame data should be pulled from the log; this is not necessarily the current time but may be any time, past or future, over the entire monitoring period of the patient 110. The response to this request is, in one embodiment, a time averaged vitals pack output 205, which contains the requested average vitals and trend information (see below), and is accepted as input at other components of the system.

One adjunct component to the vitals log table 202 is the vitals trend processor 203. When new vital signs data 112 is added to the vitals log table 202, the vitals trend processor 203 will take the new data along with any or all portions of the entirety of the preceding data and analyze, identify and store specific trends. These trends will be stored in the vitals log table 202 along with the new data on acceptance such that the trends at this time point are also available immediately for any incoming vitals request input 204. Such trend analysis, in one embodiment, includes factors like the percent change in heart rate, mean arterial pressure, dynamic predictor, cardiac output, stroke volume, and systemic vascular resistance over the last two minutes, five minutes, and ten minutes.

Figure 3:
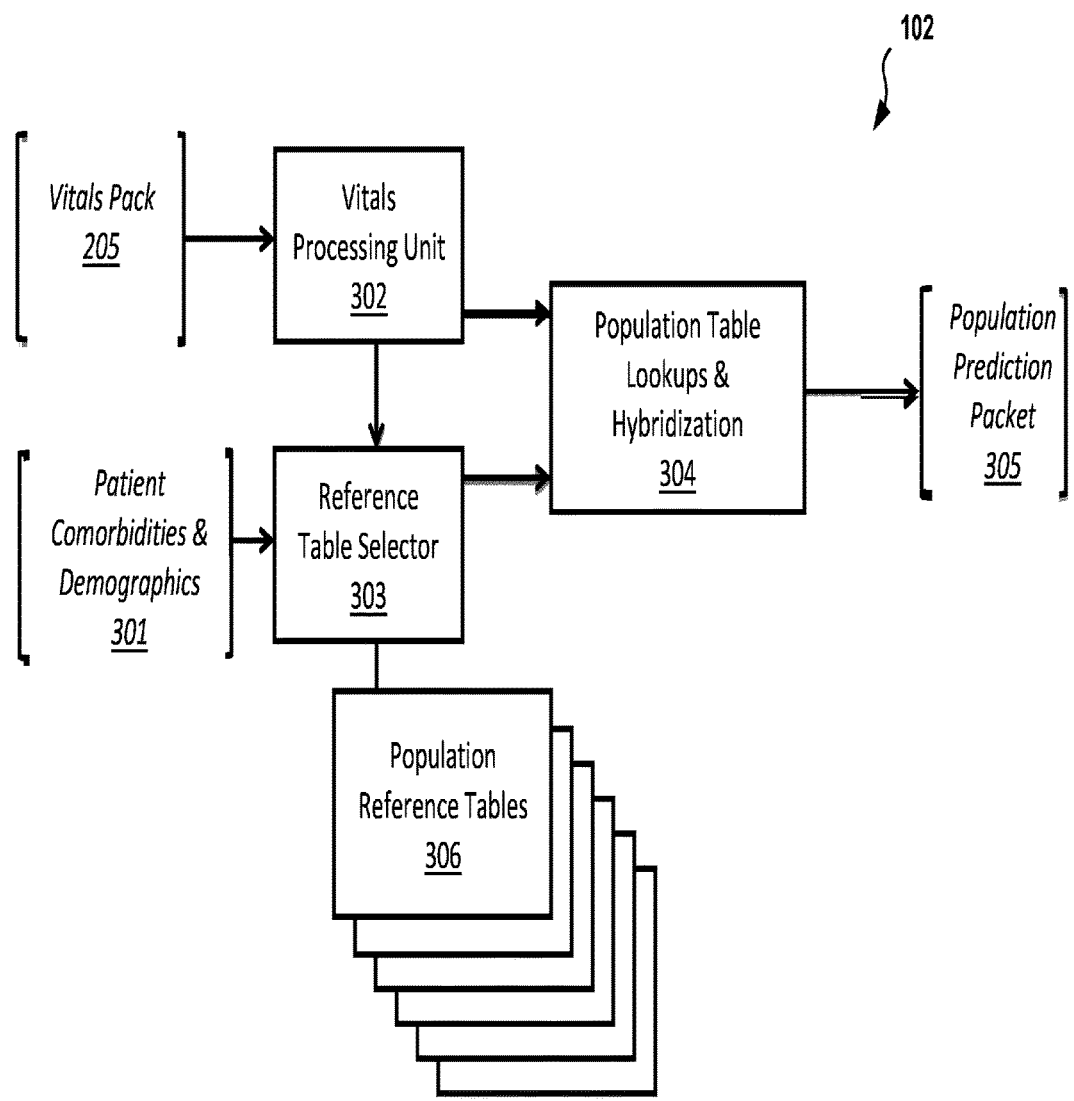
FIG. 3 illustrates details of an embodiment of a population based predictor component that can be used, for example, in the control device of FIG. 1B.

FIG. 3 illustrates details of an embodiment of a population based predictor component 102 that can be used, for example, in the control device 100 of FIG. 1B. The population based predictor component 102 receives a vitals pack output (time averaged, for example) 205 supplied by the vitals manager component 101. The vitals pack output 205 is first received by a vitals processing component 302 and distilled into specific core measures for lookup in population reference tables 306. In one embodiment of the system, these measures can include heart rate, stroke volume, systemic vascular resistance, and indications dynamic predictor(s) being utilized, but many other measures are interchangeable. For example, as cardiac output is nothing more than stroke volume multiplied by heart rate, cardiac output could be used in place of either heart rate or stroke volume with equal efficacy, and many other such replacements are feasible. The limit or requirement of four parameters necessary; other embodiments may include fewer or more. Conceptually, the purpose of this distillation of vitals pack output 205 is to succinctly characterize the patient's overall hemodynamic state during the time frame in question in as complete but concise a manner as possible for comparison with the population data (which has been previously similarly characterized and stored in the population reference tables 306).

Once the distillation and characterization of the vitals pack output 205 is completed by the vitals processing component 302, a reference table selector component 303 identifies one of a plurality of the population reference table 306 based on a comparison of (1) patient demographics and comorbidities input 301 received from the vitals manager component 101, and (2) any dynamic predictor(s) available, with similar data stored in association with the population reference tables 306. The population reference tables 306 are multi-dimensional references that link specific patient characterizations (e.g., patient demographics and comorbidities and dynamic predictors) in specific sub-populations of patients, to an expected increase in cardiac output. The patient demographics and comorbidities input 301 will be used by the population based predictor component 102 to determine which population reference table 306 is the most appropriate reference to use based on the evolving information about how patient diseases and demographic factors influence the dynamic predictors and cardiac output. In an example embodiment, an 80-year old smoker with heart failure would lead to the selection of a population reference table 306 that included only elderly smokers with heart failure, while a similar non-smoking patient would lead to a different population reference table 306 for non-smokers. The population reference tables 306 are expected to evolve as significant sub-groups are identified. Furthermore, all of the population reference tables 306 can be identified by not only the patient population represented, but by a particular dynamic predictor or predictors as well. Thus, there will be different population reference tables 306 for the example 80 year old smoker if pulse-pressure variability is available rather than plethysmograph variability, for example. Finally, more general population reference tables 306 can also be available such that a patient who does not fit the criteria of a narrow subpopulation can be referenced against the broader population.

Following the characterization of the patient state with the vitals processing component 302 and the selection of the population reference table 306 with the reference table selector component 303, a population lookup and hybridization component 304 will cross-reference the patient characterization with the chosen population reference table 306 and identify the expected increase in cardiac output for the given patient in the current state. This expected increase in cardiac output is, in the standard embodiment, the amount the cardiac output would be expected to increase in response to distinct volume of intravenous fluid over a distinct time span. For example, in one embodiment, this could be 500 ml of fluid over 10 minutes, but any volume and timeframe are possible. This predicted increase, along with a measure of the quality of the prediction (based upon the specificity of the population reference table 306 and the quality and frequency of the vitals pack output data 205 received from the vitals manager component 101) is exported in a population prediction output 305 to subsequent components of the control device 100.

Figure 4:
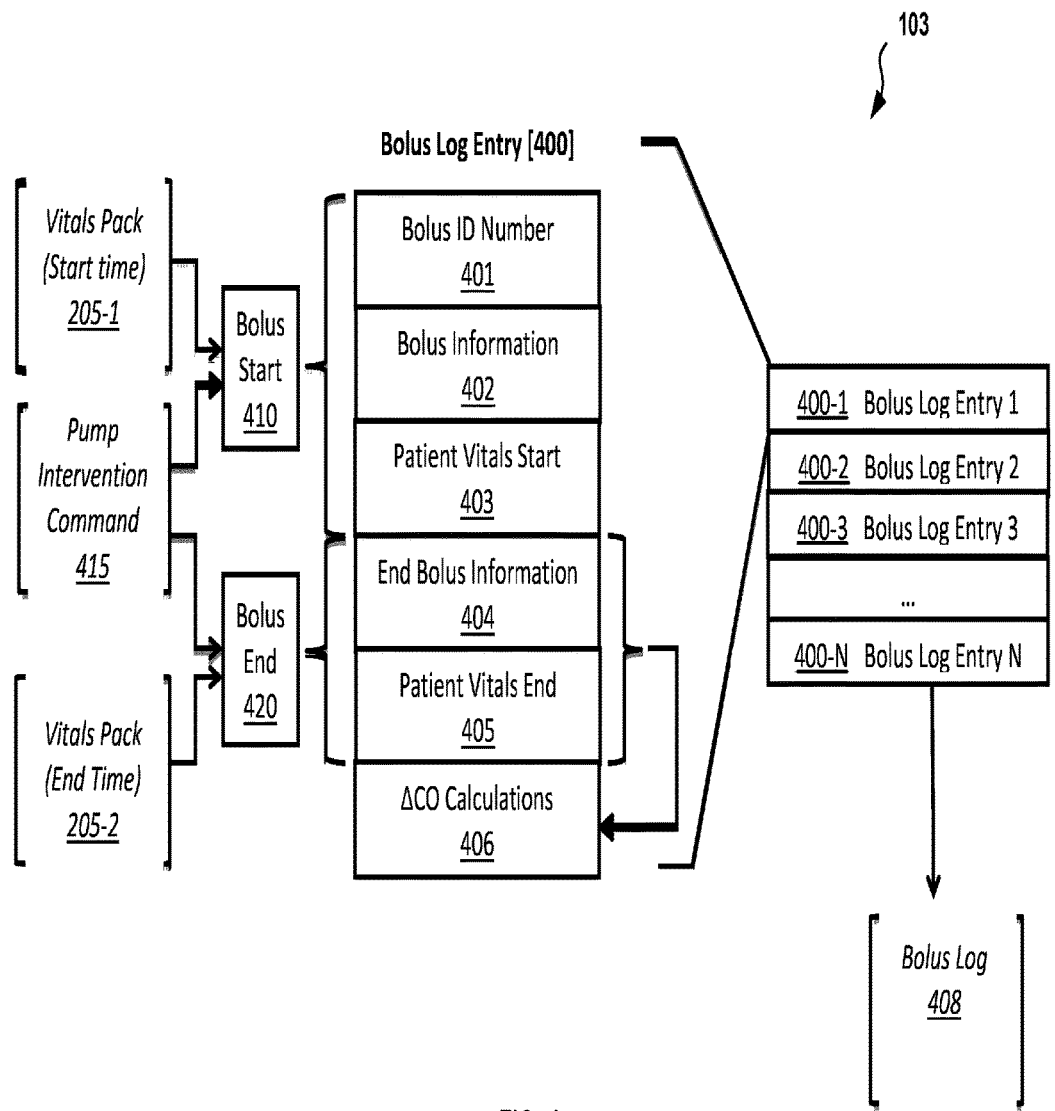
FIG. 4 illustrates details of an embodiment of a fluid bolus log component that can be used, for example, in the control device of FIG. 1B.

FIG. 4 illustrates details of an embodiment of a fluid bolus log component 103 that can be used, for example, in the control device 100 of FIG. 1B. The purpose of the fluid bolus log component 103 is to track and store bolus log entries 400 that include information associated with each distinct volume of intravenous fluid delivered by the control device 100 into a patient 110. Each bolus log can include one or more of a start time, an end time, a patient condition both before and after the bolus, and the impact of the fluid bolus on hemodynamics. Each bolus log entry 400 is initiated with the acceptance of an intervention command 415 at a bolus start interface 410. In addition each bolus log entry 400 includes a first vitals pack output 205-1 at start time received by the bolus start interface 410 from the vitals manager component 101. The first vitals pack output 205-1 includes information indicative of the vitals of the patient 110 at or prior to the start time of the fluid bolus. The intervention command 415 also includes an end time that determines the timespan over which the fluid is to be delivered. The end time information of the intervention command 415 is received by a bolus end interface 420. At the end of the bolus timespan, or shortly before or after the timespan, the bolus end interface 420 receives a second vitals pack output 205-2. The second vitals pack output 205-2 includes information indicative of the vitals of the patient 110 at or near the end of the fluid bolus.

Upon initiation of a fluid bolus, the fluid bolus log component 103 creates a new bolus log entry 400 and assigns a bolus ID number 401 to the bolus log entry 400. In addition, the intervention command includes a reason for initiation of the bolus. The fluid bolus log component 103 stores the reason for initiation of the bolus 402 in the new bolus log entry 400. The first vitals pack output 205-1 is also recorded as a patient vitals at start time 403 in the bolus log entry 400 such that the bolus log entry 400 contains a complete record of the patient vitals at the start of each fluid administration without need to access other data structures within the system. In another embodiment, first vitals pack output 205-1 is excluded from this bolus log entry 400 and merely the start time recorded, with reference made to the vitals log table 202 or another similar data store based on the start time should vital signs data be needed. The new bolus log entry 400, as identified by the distinct bolus ID 401, is left open while the fluid bolus is administered.

Following the conclusion of the fluid bolus, a waiting period can be allowed to pass before analyses of the results of the bolus are attempted. In one embodiment, this period is about two minutes, but this waiting period could be as little as instantaneous to as long as ten minutes without changing the significance of the post-analysis. Following the determined time span of the bolus, an end command of the intervention command 415 is received at the end bolus interface 420 and the fluid bolus is terminated. The fluid bolus log component 103 stores the end bolus time information 404 in the bolus log entry 400. In addition, after the determined waiting period, the second vitals pack output 205-2 is received and recorded by the fluid bolus log component 103 at a patient vitals end entry 405. In many cases, the end command of the intervention command 415 will correspond to the time upon which the target volume of the fluid bolus is achieved, but in other cases this may be a user-specified termination, an early termination due to contraindication by the patient state, or a modification of the previous bolus, among other causes. Following the recording of the end of the bolus information 404 and the post-bolus vitals in the patient vitals end entry 405, an additional set of cardiac output calculations 406 is added to the bolus log entry 400 regarding the efficacy of the bolus for future reference.

The determination of efficacy of a given bolus of intravenous fluid into the patient is now described in detail for one embodiment of the control device 100. First, a simple calculation is made to determine the absolute change in cardiac output from the beginning of the bolus to the end of the bolus:

$$\Delta CO = (CO_{end} - CO_{start})/CO_{start} \tag{1}$$

This absolute change $\Delta CO$ may not always reflect the true efficacy of a fluid bolus, however. For example, if the patient 110 was losing blood at a rapid pace, the cardiac output would steadily fall as a result. A fluid bolus given during this decline may be insufficient to actually overcome the blood loss and cause an increase in cardiac output, however it would be expected to slow the rate of decline or perhaps hold the cardiac output steady. This would still be an effective fluid bolus, though the absolute change in cardiac output would be flat or even negative and considered ineffective by this measure. Thus, a vector-based analysis can also be performed. The mean rate of change of the cardiac output of the patient over discrete timespans immediately prior to the bolus is noted and compared to the mean rate of change of cardiac output during the period of the fluid bolus. If the rate of change of cardiac output becomes less negative as a result of fluid, then this is also considered an effective bolus.

An additional method of detection of possible patient conditions confounding calculations of efficacy of a fluid bolus is the known relationship between DP, CO increase with fluid, and the change in DP with fluid.

The relationship between an increase in DP and an increase in CO in response to a 500 ml bolus in published and unpublished data has a linear regression coefficient ($R^2$) of approximately 0.39 resulting in the equation y=1.54x−1.11, where y corresponds to increase in CO and x corresponds to increase in DP [see Cannesson M, Le Manach Y, Hofer C K, Goarin J P, Lehot J J, Vallet B, et al.; "Assessing the Diagnostic Accuracy of Pulse Pressure Variations for the Prediction of Fluid Responsiveness: a 'Gray Zone' Approach." Anesthesiology, 2011. 115(2): p. 231-41]. The linear regression coefficient represents the statistical strength of the relationship between DP and CO change. This linear regression coefficient was calculated from the clinical data set. As such, it's not reflected in the equation relating y and x, but represents the "tightness" of the equation's fit to the clinical data.

The relationship between DP and DP decrease (absolute) in response to a 500 ml bolus has a linear regression coefficient ($R^2$) of approximately 0.63 for the equation y=−0.72x+4.3, where y corresponds to expected decrease in PPV and x corresponds to decrease in PPV.

Since the PPV/ΔPPV relationship is particularly strong, it can be expected that for any fluid bolus the FP value can be expected to decrease predictably. If the CO does not increase as expected in response to a bolus and the FP does not decrease within a standard deviation of the expected, there is a much higher likelihood that volume loss is to blame. If the CO does increase but the FP does decrease as expected, this is more likely to be attributable to true patient bias or deviation from expected population-based responses.

Once these calculations are completed, the cardiac output calculations 406 are stored in the bolus log entry 400 and the bolus log entry 400 is then complete. The completed bolus log entry 400 is stored as bolus log entry 400-1 in a bolus log buffer 408. The bolus log buffer 408 includes an entire list of bolus log entries 400-1, 400-2, 400-3 through 400-N which is made accessible to subsequent data processing modules (specifically the log predictor component 104 and the history analysis component 105), as well as packaged for export for sharing of the summary data.

Figure 5:
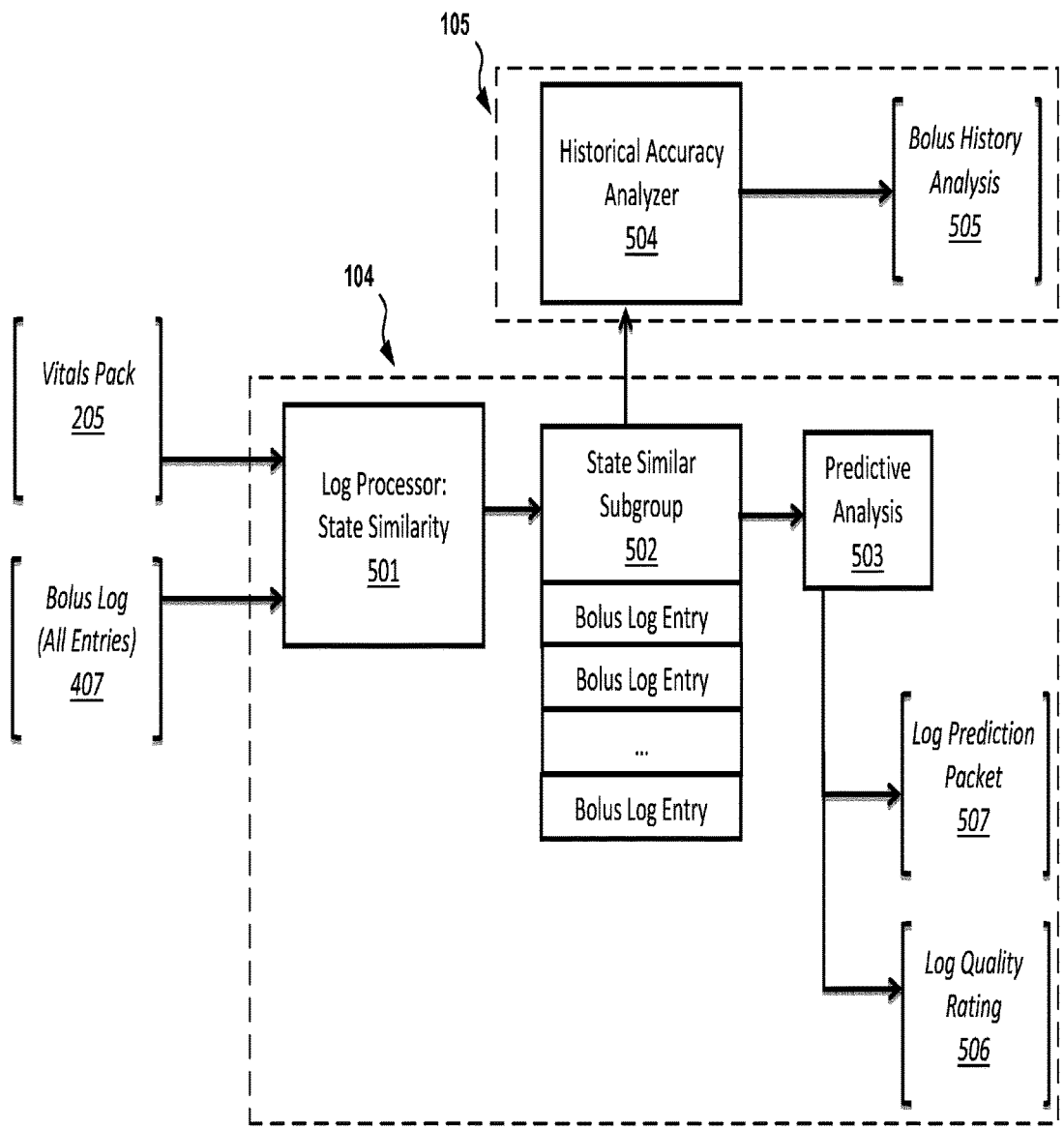
FIG. 5 illustrates details of an embodiment of a log predictor component and an embodiment of a history analysis component that can be used, for example, in the control device of FIG. 1B.

FIG. 5 illustrates details of an embodiment of a log predictor component 104 and an embodiment of a history analysis component 105 that can be used, for example, in the control device 100 of FIG. 1B. The action of these components is to: 1) in the case of the log predictor component 104, to take bolus log entries 400 from the fluid bolus log component 103 and vitals pack output data 205 from the vitals manager component 101 and determine a likely resulting change in cardiac output due to a new fluid bolus given the current patient state; and 2) in the case of the history analysis component 105, to determine the accuracy of both the population based predictor component 102 and the log predictor component 104 in predicting the correct increase in cardiac output in previous boluses in terms of both mean error and standard deviation of the mean error.

A bolus log processor component 501 receives the current vitals pack output 205 and performs a comparison of the current patient state to the patient state at the beginning of any previous boluses. This is accomplished through a process referred to herein as "state similarity" that is essentially a mathematical combination of distinct hemodynamic measures using Bayesian weights. In one embodiment, the state similarity is the square root of the sum of the squares of the differences in each measured parameter divided by the Bayesian weight of the parameter. The specific weights and hemodynamic measures used in this particular embodiment of the device are heart rate, systemic vascular resistance, stroke volume, and dynamic predictor, using weights of 0.33, 4, 0.2, and 0.1, respectively. These weights are merely one example set and may change, depending on patient population, new clinical observations, or the dynamic predictor in question. The calculation of the state similarity for these four parameters of this embodiment is made between the current state C and the previous state P as follows:

$$HRSS = HRC - HRP/0.33 \tag{2}$$

where HRC is the current heart rate, HRP is the previous heart rate and HRSS is the heart rate state similarity;

$$SVRSS = SVRC - SVRP/4 \quad (3)$$

where SVRC is the current systemic vascular resistance, SVRP is the previous systemic vascular resistance and SVRSS is the systemic vascular resistance similarity state;

$$SVSS = SVC - SVP/0.2 \quad (4)$$

where SVC is the current stroke volume, SVP is the previous stroke volume and SVSS is the stroke volume similarity state; and $$DPSS = DPC - DPP/0.1 \quad (5)$$

where DPC is the current dynamic predictor, DPP is the previous dynamic predictor and DPSS is the dynamic predictor similarity state. The resulting total state similarity measure of quality "SSTotal" is calculated as follows:

$$SSTotal = 100 - HRSS - SVSS - SVRSS - DPSS \quad (6)$$

The state similarity parameters HRSS, SVRSS, SVSS, DPSS and SSTotal and the corresponding bolus log entry are stored in a state similarity subgroup buffer 502. Entries in the state similarity bolus log subgroup buffer 502 that exhibit a quality measure SSTotal greater than a "similar" threshold level, and are of a sufficient volume and given over a timespan appropriate to draw meaningful conclusions from, are passed on to a predictive analysis component 503. Entries in the state similarity bolus log subgroup buffer 502 that exhibit a quality measure SSTotal greater than a "highly similar" state similarity threshold level are given added weight. In a typical embodiment, the "similar" and "highly similar" state similarity threshold levels are 50 and 75 respectively. Entries in the state similarity bolus log subgroup buffer 502 that exhibit quality measures SSTotal that do not meet these thresholds are discarded. In this way the prediction made by the log predictor component 104 is specific to the current global hemodynamic state of the patient 110, such that if the patient 110 changes dramatically over the course of care, previous intervention results are not assumed to be comparable in the new state.

The log processor component 501 can start the state similarity analysis of the bolus log entries 400 with the most recent entries and work backward in time. As previous bolus log entries 400 meet the predetermined state similarity thresholds, a running tally of the total state similarity of entries found is kept. When this tally reaches another threshold level, the log processor component 501 stops further state similarity analysis and retains only the entries already captured. In this way, the algorithm manifests both a memory of its past efficacy as well as a 'forgetfulness', such that if some aspect of the patient changes in a way that truly alters the patient response to fluid the system will not be permanently biased by the early results but rather will be progressively more influence by the recent results of interventions.

As an example of this behavior, take a patient in steady state during surgery. The patient cardiac output is 4.5 and the system attempts a fluid bolus. The cardiac output improves to 5.6, a 21% increase. This is considered effective by the system and is recorded as such in one of the bolus log entries 400. Subsequently the patient has some ischemic heart injury and the cardiac output falls back to 4.5, not because of hypovolemia but because of a loss of inotropy. The system will likely attempt another bolus in this state as the previous one was successful, but in this instance there will be no improvement in cardiac output because the intravascular volume is already maximized. Were it not for the forgetful component of the state similarity analysis of the bolus log entries 400, the system might continually operate using the initial success indefinitely and thus continue to deliver fluid inappropriately. The emphasis of recent activity and results over more distant activity and results ensures that ineffective interventions are rapidly phased out.

Once the entries in the state similarity bolus log subgroup buffer 502 that are applicable to the current patient state are selected by the log processor component 501, a predictive analysis is performed on the subgroup buffer 502 by a predictive analysis component 503. The predictive analysis calculates a running average of the change in cardiac output recorded for the entries stored in the subgroup buffer 502. In one embodiment, the entries in the subgroup buffer 502 are weighted in the running average calculation by their quality measure SSTotal as determined by the log processor component 501, such that the higher the SSTotal of a previous bolus to the current patient state the more weight the prediction will carry in the combined running average. The output from predictive analysis component 503 is a log prediction packet 507 and a quality rating packet 506 that includes information about the total number of entries in the subgroup and the corresponding state similarity quality measures SSTotal.

Referring again to FIG. 5, the subgroup buffer 502 selected by the log processor component 501 is also passed into the historical accuracy analyzer 504 of the history analysis component 105. The historical accuracy analyzer 504 reviews each of the selected bolus log entries 400 contained in the subgroup buffer 502 and compares the cardiac output increase predicted by the population based predictor component 102 and by the log predictor component 104 to the actual increase seen in the patient and calculates the average error and standard deviation of the error for each respective predictor. This information is exported and stored in a bolus history analysis buffer 505.

Figure 6:
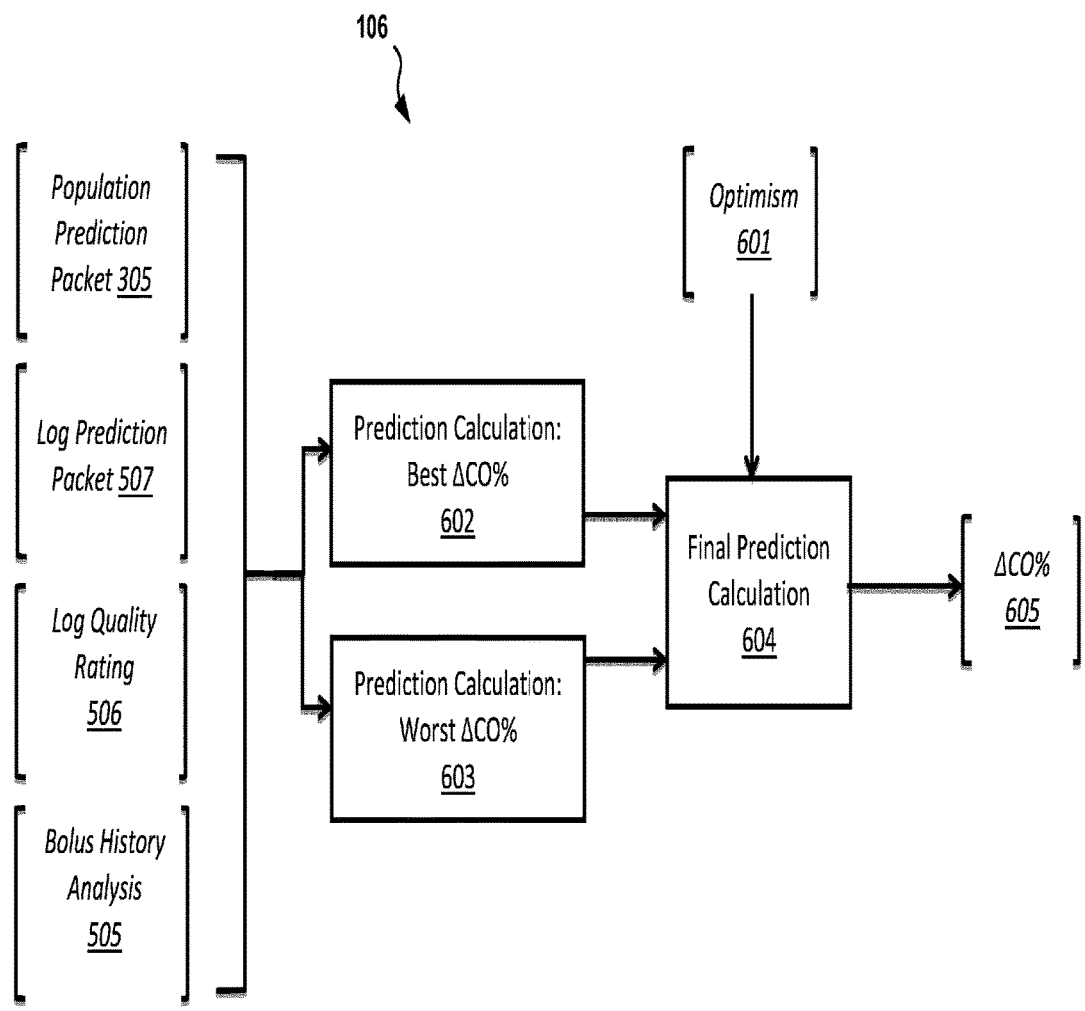
FIG. 6 illustrates details of an embodiment of a prediction engine that can be used, for example, in the control device of FIG. 1B.

FIG. 6 illustrates details of an embodiment of the prediction engine 106 that can be used, for example, in the control device 100 of FIG. 1B. The prediction engine 106 receives inputs from all of the other predictive components. Specifically, the prediction engine 106 receives the population prediction output 305 from the population predictor component 102, the log prediction packet 507 and the quality rating packet 506 from the log predictor component 104, and the bolus history analysis buffer 505 from the history analysis component 505. The prediction engine 106 uses these inputs to generate a final combined predicted cardiac output change for the current state of the patient 110.

The process begins with the prediction engine 106 receiving a population prediction output 305, a log prediction packet 507, a log quality rating 506, and a bolus history analysis 505. The predictions included in the log prediction packet 507 and the population prediction output 305 are adjusted by the mean error value contained in the bolus history analysis buffer 505 for the respective components. Then the standard deviation of error is both added and subtracted from each component to yield two predictions for each component representing the top and bottom of the range of increase of cardiac output expected. The top and bottom predictions from a first one of the predictive components is averaged with the top and bottom predictions from the second one of the predictive components using the inverse of the standard deviations of each to weight the averages. This results in the narrower standard deviation of the two being given more weight in the resulting value. This results in two final predictions, one for the top and one for the bottom. In the embodiment shown, a best case prediction component 602 calculates the top or greatest predicted change in cardiac output and a worst case prediction component 603 calculates the bottom or least predicted change in cardiac output.

A final prediction component 604 combines the best case prediction and the worst case prediction to determine the final predicted change in cardiac output 605. In the embodiment shown, an "optimism" input 601 is provided to the final prediction component 604. In this embodiment, the optimism input 601 is a user-defined value between zero and 100 that is used to determine the final predicted change in cardiac output 605 made by the final prediction component 604 within the best case and worst case values determined by the best and worst case prediction components 602 and 603, respectively. A value of 100 of the optimism input 601 results in the best case predicted change, while a value of zero results in the worst case predicted change in cardiac output. Values between zero and 100 will result in values between the best and worst case values (e.g., linearly interpolated values). The final predicted change in cardiac output 605 is then output. In another embodiment, the optimism input 601 is a fixed value of 100, 75, 50, 25, 0, or some value in-between determined in advance or hard-coded into the algorithm. In yet another embodiment the optimism input 601 is a range of values between the lower end of zero and the upper end of 100.

Figure 7:
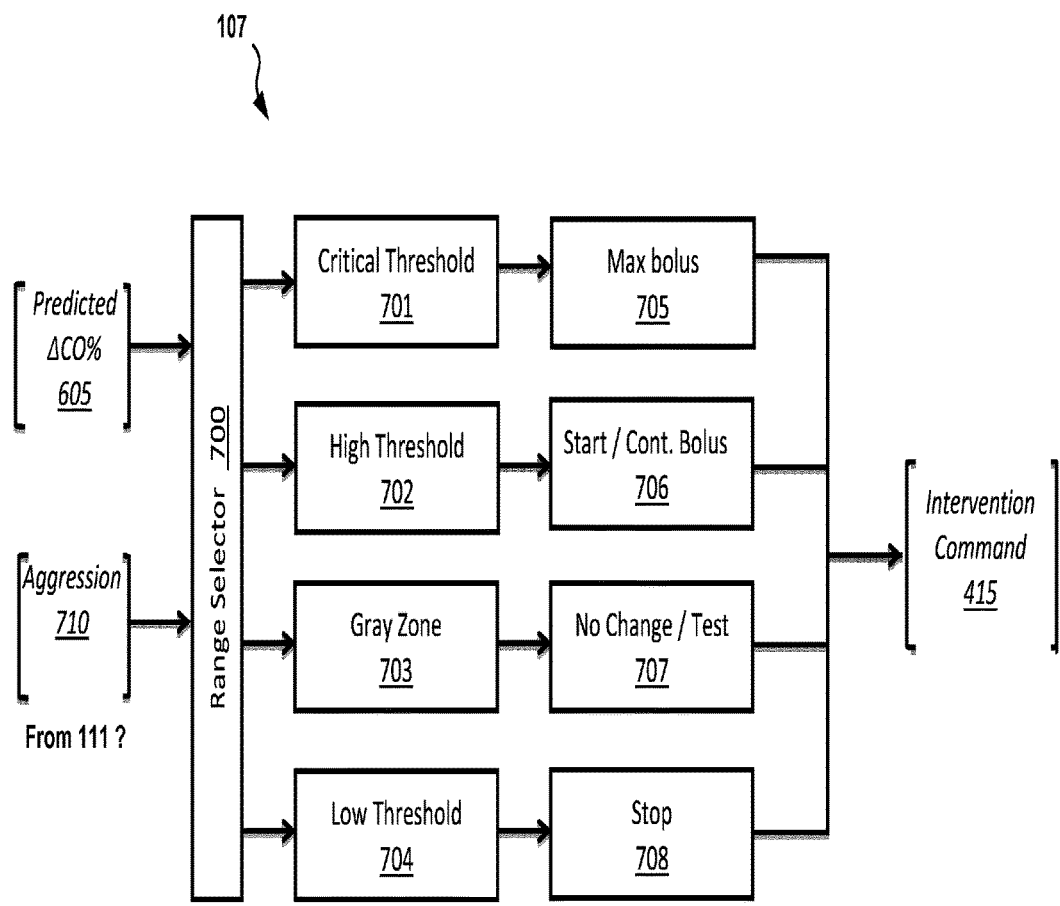
FIG. 7 illustrates details of an embodiment of an intervention decision component that can be used, for example, in the control device of FIG. 1B.

FIG. 7 illustrates details of an embodiment of an intervention decision component 107 that can be used, for example, in the control device 100 of FIG. 1B. The intervention decision component 107 receives the final predicted change in cardiac output 605 determined by the prediction engine 106, and in conjunction with an aggression rating 710 determines an action to be taken by the control device 100. In one embodiment the aggression rating is a user-specified value within the range −10 to +10, inclusive. In another embodiment, the aggression rating 710 can be fixed, or may have a different range. Regardless of the way the aggression rating 710 is determine, the aggression rating 710 is used to generate the intervention command 415 that is provided to the pump manager component 108.

The final predicted change in cardiac output 605 (given in percentage increase in cardiac output in this embodiment) received by the intervention decision component 107 is received by an intervention range selector 700 and compared to decision ranges to determine the appropriate course of action. In one embodiment, there are four such ranges, though more or less may be present in other embodiments. The lowest such range in this embodiment is the low threshold zone 704, in which the administration of fluid is likely to be at best not helpful and at worst detrimental. A second range is the gray zone 703, in which the outcome of fluid administration is either indeterminate or mixed. A third range is the high threshold zone 702 in which fluid is likely to increase cardiac output significantly. A fourth range is the critical threshold zone 701 in which fluid is almost certain to have a substantial positive impact. In this embodiment, the percentage increase in cardiac output for these zones are 0-7% for the low threshold zone 704, 8-14% for the gray zone 703, 15-25% for the high threshold zone 702, and 25% and greater for the critical threshold zone 701.

As indicated in FIG. 7, each of these zones corresponds to an action or set of actions 705, 706, 707 or 708 to be taken by the control device 100. The specific response to a given zone will depend on the embodiment of the system and the number of zones. In the embodiment illustrated in FIG. 7, the response taken in each of the zones is as follows: in the low threshold zone 704 the response is to stop any ongoing infusion and continue monitoring 708; in the gray zone 703, the response is to continue whatever action is currently taking place 707, and in some cases to deliver a test bolus (see below); in the high threshold zone 702, the response is to initiate a fluid infusion, or to continue an infusion if already running 706; and in the critical zone 701, the response is to accelerate any ongoing infusion to the maximum system rate or start such an infusion if not already active 705. The final action is sent as an intervention command 415 to the pump manager 108.

The volumes and rates of the infusions being started upon intervention are specific to the embodiment of the control device 100 and depend on the characteristics of the pumps 109. In an embodiment for use in a human patient 110, a high threshold zone 702 infusion response 706 is 250 ml of fluid, given over a time span of 5-10 minutes depending on the pump capacity, and a critical zone 701 infusion 705 is 500 ml of fluid given over 5-10 minutes depending on the pump capacity. In other embodiments these volumes may be modified as well as the time spans of delivery.

Again referring to FIG. 7 and the preferred embodiment of the device, in some cases a "test bolus" will be delivered by the pump in the Gray Zone to determine whether or not fluid is likely to be beneficial. This test bolus can be 100 ml of fluid delivered over a time span of between one and ten minutes. Specifically, when a patient is determined to be in the gray zone, and there are no high quality bolus log entries 400 as determined by the state similarity processor 501 within a specified timeframe, a test bolus is initiated. In one embodiment this timeframe is two, three, four, six, ten, or twelve hours.

With further reference to FIG. 7, the aggression rating 710 is used to modify the zone boundaries during operation of the control device 100. A positive aggression rating 710 will lower the percentage change in cardiac output of the boundaries, thereby making the control device 100 more likely to deliver fluid for any given prediction by the system. A negative aggression rating will raise the percentage change in cardiac output of the boundaries, and thereby make the control device 100 less likely to deliver fluid for any given prediction by the system. The boundaries may, in one embodiment, be raised by a fixed value for each point of the aggression rating 710 and in another embodiment may be multiplied or divided by a value for each point of the aggression rating 710. The aggression rating 710 is, in one embodiment, determined by a supervisor during operation of the control device 100.

In another embodiment, the intervention decision component 107 may also include a direct input from the vitals manager component 101 through which the intervention decision component 107 receives instantaneous or short-time-averaged vital signs. In this embodiment the intervention decision component 107, in addition to making recommendations and decisions about IV fluid administration also makes recommendations and decisions about medication administrations.

In such an embodiment, vasoactive medications may be recommended to the supervisor if deemed appropriate, or, in one embodiment, delivered to the patient 110 directly by the system after supervisory approval or autonomously.

Figure 8:
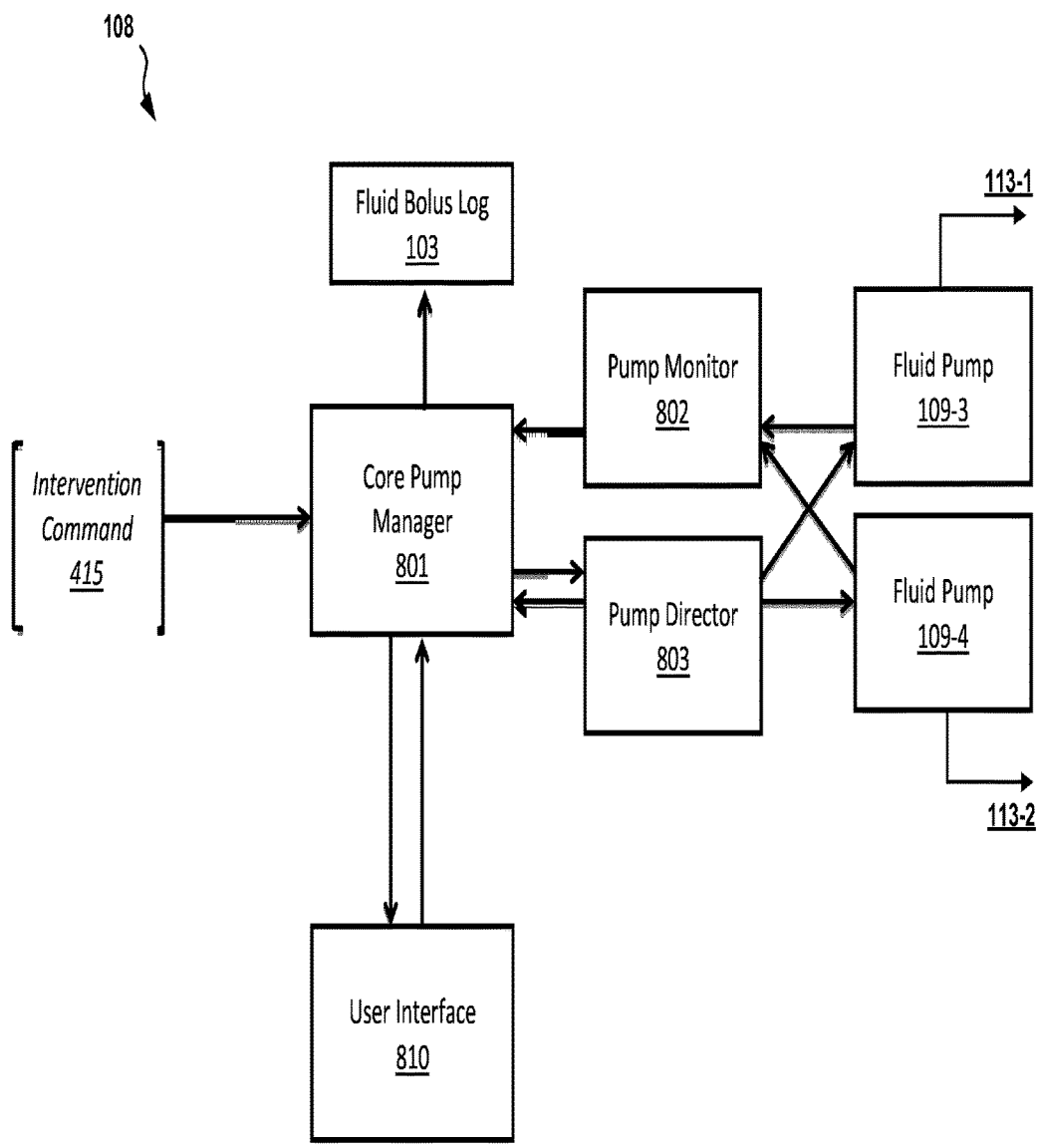
FIG. 8 illustrates details of an embodiment of a pump manager component that can be used, for example, in the control device of FIG. 1B.

FIG. 8 illustrates details of an embodiment of a pump manager component 108 that can be used, for example, in the control device 100 of FIG. 1B. As discussed above, the function of the pump manager component 108 to is to coordinate fluid pump activity, to monitor the fluid pumps 109 to ensure proper response to commands issued to the fluid pumps 109, and to interact with a user interface 810 when appropriate. In one embodiment, the pump manager component 108 is the only component of the control device 100 that receives direct instructions in the form of actionable commands from the user interface 810.

The monitoring and control functions of the pump manager component 108 are provided by interaction between a core pump manager component 801, a pump director component 803, the fluid pumps 109-3 and 109-4, and a pump monitor 802. Any desired pump action communicated from the user interface 810 or received in an intervention command 415 from the intervention decision component 107 is received by the core pump manager component 801 and relayed to the pump director component 803. The received pump actions contain explicit information and formatting enabling the core pump manager component 801 to communicate those actions to the specific fluid pumps used in each particular embodiment. The pump director component 803 will confirm that the commands are received and accepted by the fluid pumps 109-3 and/or 109-4, but the pump director component 803 does not track the action of the pumps 109-3 and 109-4 beyond this step. If the commands are rejected, not acknowledged, or any other communication error arises between the pump director component 803 and the fluid pumps 109-3 and 109-4, this is communicated back to the core pump manager component 801 along with the nature of the error.

One feature of operation of the pump manager component 108 is that any command sent to the fluid pumps 109-1 or 109-2 for delivery of an IV fluid bolus 113-1 or 113-2 contains both a rate and a volume for delivery. Furthermore, the fluid pumps 109 themselves can be designed such that only a command containing both elements is accepted by the pumps. This feature can ensure safety to the patient 110 should communication between the system and the fluid pumps fail for any reason, and further, should the fluid pumps 109, upon loss of communication with the rest of the system, fail to halt active infusions and enter a standby mode until communication is reestablished, they will automatically stop infusing fluid at the completion of the dictated bolus volume. Thus, the fluid pumps 109 are not left indefinitely in an infusing mode due to loss of system communication which could result in over-administration of fluid and pose a safety risk to the Patient.

The pump monitor component 802 is responsible for the ongoing supervision of the fluid pumps 109 following the initial issuance of a command by the pump director component 803. The pump monitor component 802, at system specified time intervals, queries the fluid pumps 109 and requests an update on their status. The time interval, in one embodiment, may be 100 seconds, 10 seconds, 1 second, 1/10th seconds, 1/100th seconds, or 1/1000th seconds. The status update, in one embodiment, can contain the current pump state (on, off, waiting, infusing, alarm, error) along with detailed information about the amount of volume given in the current infusion (if active), the rate of the current infusion (if active), the total volume given to this patient, the back pressure in the infusion tubing, the available volume to infuse (if present), the nature of the fluid available to infuse (if present), and detailed alarm information (if active). This information is organized and transmitted to the core pump manager component 801.

The core pump manager component 801, as previously described, is responsible for coordination of all pump activity involving the intervention commands 415 received from the intervention decision component 107 or from other parts of the system such as the user interface 810. Commands are passed into the pump director component 803 for transmission to the fluid pumps 109. If the intervention commands 415 are accepted no further action is needed. If a command fails due to any of the communication errors discussed above, or for any other reason, this failure is relayed back to the core pump manager component 801 by the pump director component 803 for further action. If the nature of the failure may be temporary, for example, a failure of acknowledgement of the command by one of the fluid pumps 109, the core pump manager component 801 may attempt to repeat the command one or more times before taking other action. In other failures that are not likely to be resolvable by the system (for example, air detected in the pump tubing or similar failure alarms, or a pump hardware failure), then an alarm condition may be set by the core pump manager component 801 indicating the nature of the alarm and relayed to the user interface 810 for communication with and input from the human supervisor.

In the event of an alarm condition specific to a single fluid pump 109, in an embodiment that possesses two or more fluid pumps 109, the core pump manager component 801 may continue operating and attempt to compensate for the fluid pump 109-3 that has failed with the other available fluid pump 109-4 or vice-versa until the condition can be rectified by the supervisor or the condition resulting in the alarm is otherwise resolved. In the event of an alarm condition affecting the entire system, the monitoring of vital signs or the quality of information received into the vitals manager component 101, or in an embodiment with only one fluid pump 109, the core pump manager component 801 will attempt to halt active infusions if possible and will standby until the alarm condition is resolved satisfactorily by the supervisor. Any desired actions dictated by the system in this state will be ignored.

In addition to passing commands on to the pump director component 803, the core pump manager component 801 also verifies the data received from the pump monitor component 802 to make sure the actual state of the fluid pumps 109 is consistent with the state dictated by the last command provided by the pump director component 803. If the fluid pumps 109 are in a state different from the expected state but communication between the fluid pumps 109 and core pump manager component 801 is intact, the core pump manager component 801 will attempt to issue corrective commands to the pump director component 803 to place the fluid pumps 109 into the correct state. If this fails to correct the discrepancy then a global alarm condition can be set and communicated to the user interface 810 and further pump commands ignored until the alarm condition is resolved.

In some instances, the state of one or more of the fluid pumps 109 will be affected by the last command issued by the pump director component 803 in an expected manner. For example, if the pump director component 803 issues a command to infuse 500 ml of fluid over 10 minutes, after this infusion completes the fluid pumps 109 will return to standby mode. This is the expected progression of the last issued instruction and as such will be anticipated by the core pump manager component 801 and treated as consistent with the last issued command. Thus, no alarm condition would result.

Referring again to FIG. 8, the core pump manager component 801 is also configured, in a decision-support or physician verification mode, for communication of desired actions to the user interface 810 for verification by the supervisor. In this mode, any intervention command 415 received is not acted on by the core pump manager component 801 autonomously. Instead, the intervention command 415 is conveyed to the user interface 810 and displayed to the user along with the option to accept or reject the command. If the command is rejected the core pump manager component 801 takes no further action and will ignore additional identical commands until such a time as the command changes or a pre-determined time span passes. Depending on the embodiment, this time span can be between one and sixty minutes, for example. If the command is approved then the core pump manager component 801 passes the command along to the pump director component 803 for conveyance to the fluid pumps 109.

The core pump manager component 801 may also receive specific override commands from the supervisor. These are described in detail later. Should the core pump manager component 801 receive such an override command that command is also communicated to the fluid bolus log component 103 in the form of an intervention command 415, for proper registration of the intervention command as a bolus log entry 400 in the bolus log buffer 408.

Referring again to FIG. 8, in one embodiment, the pump director component 803 may be absent from the operation of the system. In this embodiment, the system has no direct control over the fluid pumps 109 whatsoever. Instead, the operation of the fluid pump(s) 109 is handled by the supervisor directly through the fluid pump(s) own control interface(s). The activity of the fluid pump(s) 109 is relayed back to the core pump manager component 801 through the pump monitor component 802, and this information is passed along to the fluid bolus log component 103 in order to track the administration of IV Fluid 113 into the patient 110. Meanwhile, the decisions of the control device 100 are relayed to the supervisor through the user interface 810 as recommendations of care. These recommendations may be displayed to the supervisor in graphical or numeric fashion, the main point being to convey the degree of fluid responsiveness (or predicted efficacy of additional fluid) in the patient 110 by the system.

Figure 9:
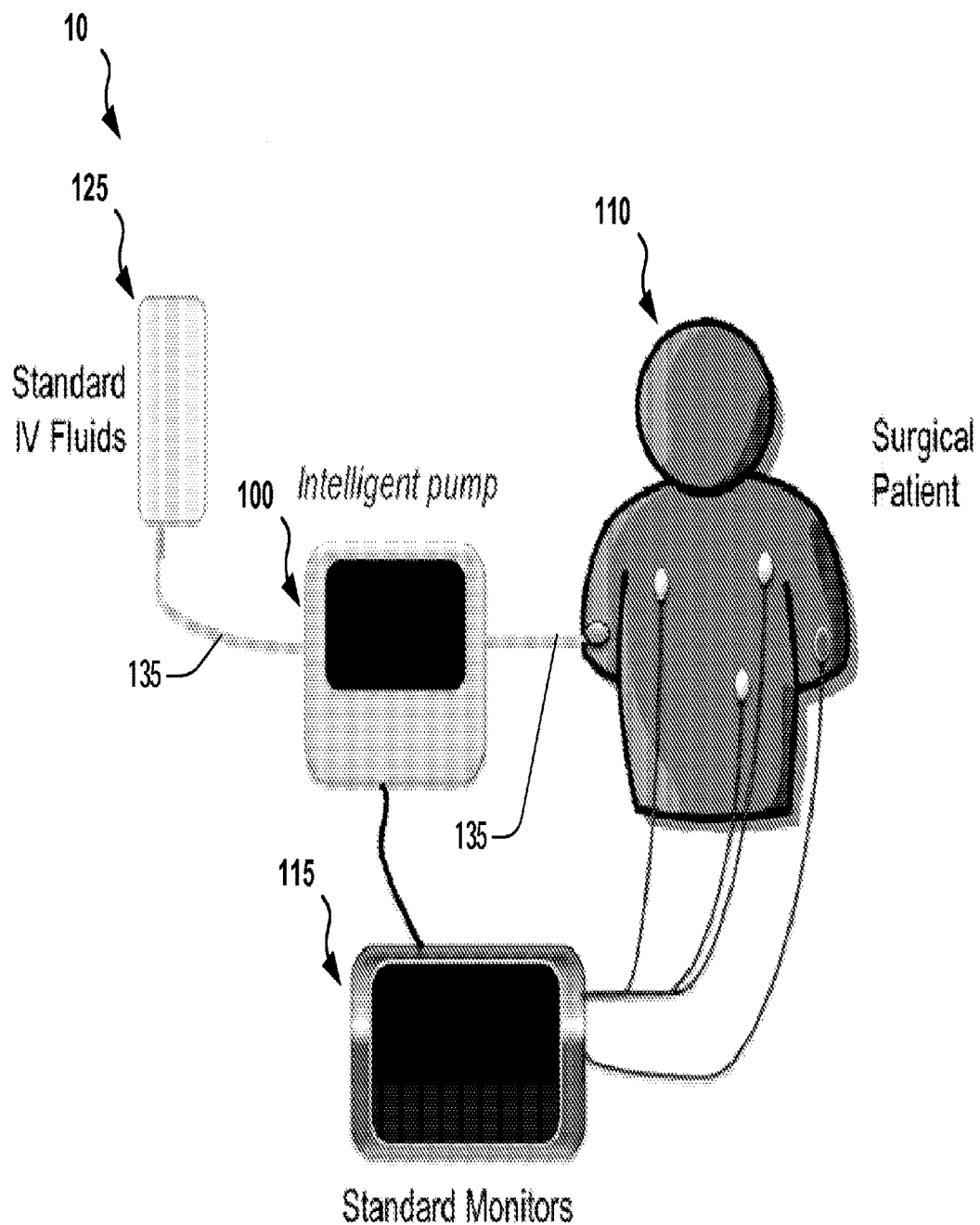
FIG. 9 illustrates details of another exemplary patient-adaptive hemodynamic management system in accordance with the disclosure.

FIG. 9 illustrates details of another exemplary patient-adaptive hemodynamic management system 10 in accordance with the disclosure. In this embodiment, an IV bag 125 of fluid is hung above the control device 100 and, using purposed tubing 135 already primed and inserted into the control device 100 tubing 135, channel and then connect to standard IV access points on the patient 110 or other tubing, delivered by the control device 100 as described throughout the disclosure. Vital signs are delivered to the control device 100 through a physical connection with standard operating room clinical monitors 115 in the illustrated embodiment of FIG. 9. In another embodiment the clinical monitors 115 are replaced with monitors integrated into the control device 100 and connected to the patient 110, or integrated into the control device 100 and in communication with wireless leads and contacts placed on the patient 110. In another embodiment the vital signs are communicated to the control device 100 from other monitors over a wireless network such as Bluetooth or other wireless communication protocols. In yet another embodiment, the vital signs are monitored from a distance by devices not in physical contact with the patient and subsequently communicated to the control device 100.

Again referring to FIG. 9, in the illustrated embodiment there one IV bag 125 fluid shown and one line of tubing 135 is shown connecting the IV bag 125 to the control device 100. In another embodiment, two, three, or four different IV bags 125 each with its own tubing run through a dedicated channel in the device, and each IV bag 125 containing different fluids may be used. In such an embodiment, the user of the control device 100 may specify which bag should be used first, second, third, or so on by the system. In another embodiment of the control device 100, the control device 100 is made aware of what the individual fluid bags contain and will determine which fluid is appropriate based on internal rule sets.

In another embodiment of the management system 10, one of the clinical monitors 115 provides a continuous or intermittent measure of patient 110 hemoglobin concentrations. In another embodiment of the management system 10, one of the monitors 115 provides a measure of mixed central venous oxygen saturation or regional central venous oxygen. In yet another embodiment of the management system 10 one of the monitors provides a continuous or intermittent measure of regional or global tissue oxygen delivery or utilization.

In another embodiment of the management system 10, the control device 100 is coupled to either oxygen delivery, tissue oxygenation or utilization, blood hemoglobin concentration, mixed central venous oxygen saturation, or regional venous oxygen saturation, and one of the fluids available to the control device 100 is an oxygen carrying product such as, for example, whole blood, packed red blood cells, salvaged patient blood from the surgical field, artificial blood products or an oxygen-carrying blood substitute. In another embodiment, based on the described setup, the management system 10 may elect to give such an oxygen carrying product instead of other available fluids in the event oxygen delivery to tissues is determined to be inadequate. This may occur independently of decisions made regarding the benefit of fluids alone as determined by the components described above.

Figure 10:
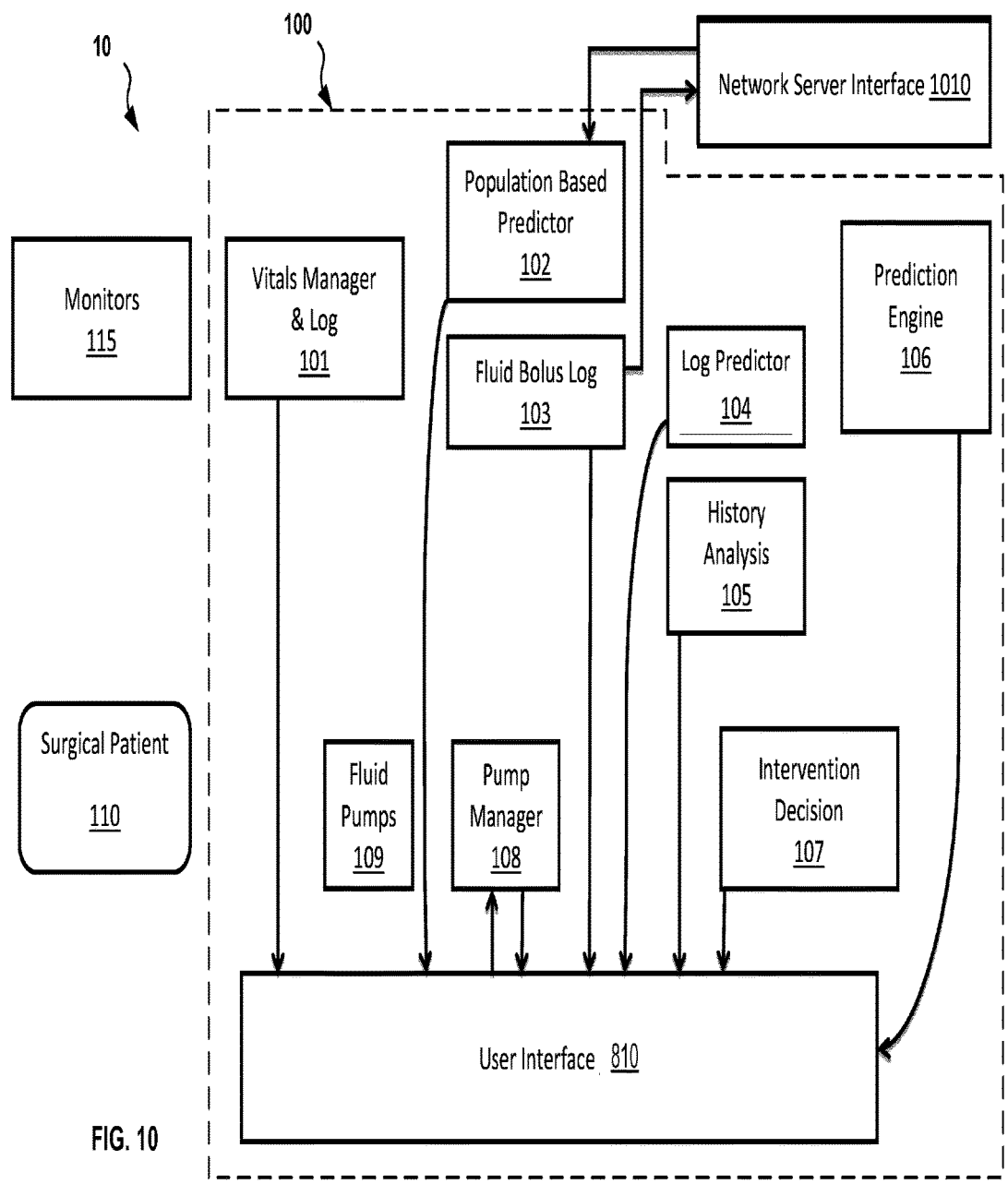
FIG. 10 illustrates information flow between various components of the patient-adaptive hemodynamic management system of FIG. 1A.

FIG. 10 illustrates information flow between various components of the patient-adaptive hemodynamic management system 10 of FIG. 1A. FIG. 10 shows the same components as FIG. 1, but in this illustration the connections between the components are not shown. Instead the connections between the system components and the user interface 810 and a network server interface 1010 are demonstrated.

As illustrated in FIG. 10, each component of the management system 10 has outputs to the user interface 810. These outputs may provide data that can be displayed or not displayed to the supervisor depending on the particular embodiment and implementation of the control device 100. In the embodiment shown, the only active input from the user interface 810 to components of the control device 100 is an input the pump manager component 108, specifically the core pump manager component 801. This input carries, in one embodiment, the approval or rejection of recommended intervention commands 415 as determined by the supervisor. Additionally, in another embodiment, this input carries supervisor directed override commands to either halt the fluid pump(s) 109 or to initiate a new infusion. These override commands will either persist indefinitely until cleared by the supervisor or will timeout after a predetermined timespan at which point the affected fluid pump 109 will revert to the previous mode of operation.

In one embodiment, an additional supervisor override command is a "line flush" command. When the fluid pumps 109 are already actively infusing fluid, this line flush command has no effect. When the fluid pumps 109 are in a standby state, the line flush command will cause the fluid pumps 109 to briefly activate and infuse, for example, 2, 5, 8, 10, or 15 ml of fluid depending on the total volume of fluid present in the IV fluid set in the current configuration. After this volume of fluid is infused, the fluid pumps 109 return to a standby state. The purpose of the line flush command is to drive the column of fluid present in the line into the patient 110 such that any medication administered into the line downstream of the fluid pumps 109 will also be flushed into the patient 110.

An additional supervisor override command present in another embodiment of the control device 100 is a "test bolus" command. When the fluid pumps 109 are in a standby mode, the test bolus command causes a new fluid bolus to be initiated. The volume and time of this bolus are, in one embodiment, 50 ml, 100 ml, 150 ml, 200 ml, or 250 ml of fluid given over 1, 2, 3, 4, 5, 10, or 15 minutes. If a new infusion command is received (and accepted by the supervisor, if necessary), during this test bolus, the test bolus is stopped and the new bolus is started. Otherwise the test bolus will run to completion and then halt.

Referring again to FIG. 10, two components of the system interact with the network server interface 1010, the fluid bolus log component 103 and the population based predictor component 102. These interactions may not occur continuously during routine operation of the system, nor are they required as a component of the system.

In one embodiment, specific information is exchanged between the control device 100 and the network at the beginning and end of operation, or at preset time intervals. Specifically, the bolus log 408 and the patient demographics and comorbidities 301 are packaged and communicated to other networked components via the network server interface 1010. This data includes the details of the bolus log 408, significant patient disease states, and non-identifying demographic data such as patient age, height, weight, and gender. This data may not contain, in one embodiment, any information making specific identification of the source patient possible through the dataset.

The information communicated via the network server interface 1010 is received by other networked control devices 100 and processed and reorganized into population reference tables 306 which may be specific to a pertinent patient subset or to the population in general. Subsequently, at device startup time or at preset time intervals, the networked control devices 100 can update their own internal population reference tables 306 through the network server interface 1010. In this way, the population reference tables 306 will evolve over time as increasingly detailed population data becomes available for any given patient population.

The network server interface 1010 may connect to other networked servers and/or control devices 100 over any of a number of forms of electronic communication, including but not limited to Ethernet, Wireless TCP/IP, Bluetooth, Cellular technologies, or removable media formats.

Figure 11:
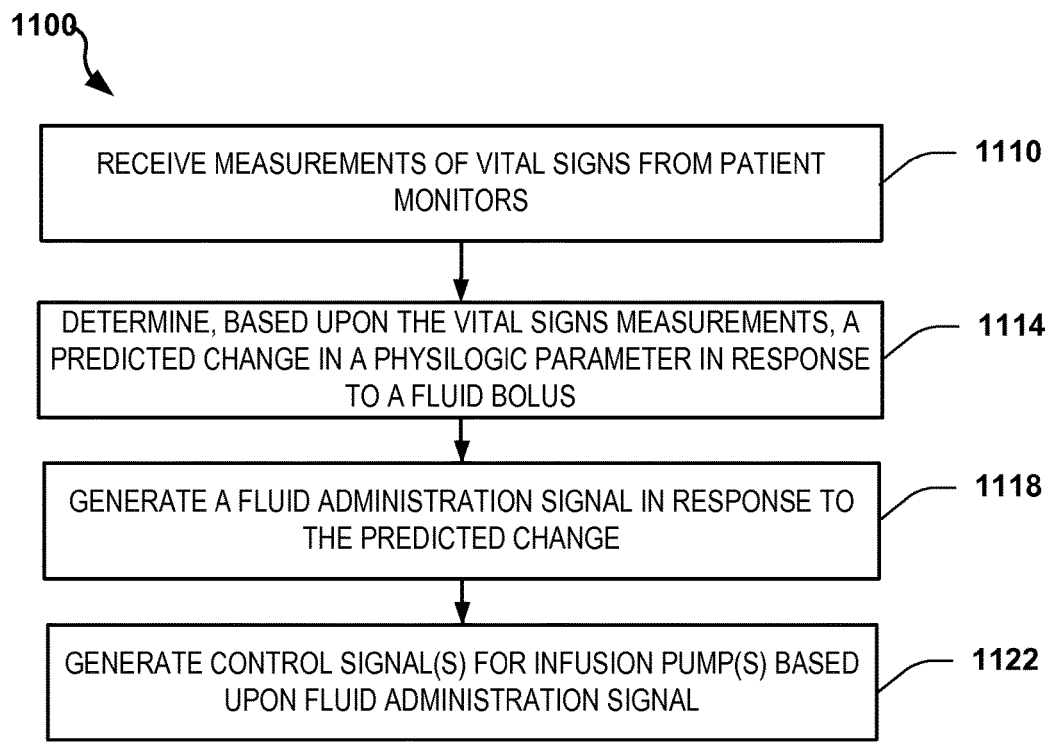
FIG. 11 is a flowchart depicting an exemplary method of providing patient-adaptive hemodynamic management in accordance with the disclosure.

Attention is now directed to FIG. 11 which is a flowchart depicting an exemplary process 1100 of providing patient-adaptive hemodynamic management in accordance with the disclosure. The process 1100 can be performed by the patient-adaptive hemodynamic management system 10 illustrated in FIGS. 1A and 1B including the control device 100 illustrated in FIGS. 2-8. The process 1100 is exemplary only and not limiting. The process 1100 can be altered, e.g., by having stages added, removed, rearranged, combined and/or performed concurrently.

The process 1100 will be described in reference to the control device 100 of FIGS. 1A, 1B and FIGS. 2-8. The process 1100 begins at stage 1110 where the vitals manager component 101 receives measurements of vital signs from clinical monitors 115. The received vital signs can include physiologic processes such as cardiac output, stroke volume, heart rate, blood pressure and arterial pressure for example.

Upon receiving the vital signs, the process 1100 continues at stage 1114 where the control device 100 determines, based at least in part upon the vital signs measurements, a predicted change in a physiologic parameter in response to a fluid bolus. The predicted change can be predicted in part by the population based predictor component 102 based on population statistics, and/or in part by the log predictor component 104 and/or, in part by the history analysis component 105 as discussed above. In addition, the population based prediction portion, the bolus log prediction portion and the history analysis predictions can be combined by the prediction engine 106 as discussed above. The physiologic parameter can include one or more of cardiac output or stroke volume of the patient 110.

Upon predicting the change in the physiologic parameter, the process 1100 continues at stage 1118 where the intervention decision component 107 generates a fluid administration signal in response to the predicted change. The administration signal can be a signal to stop a fluid bolus currently being administered, to continue a current action and continue to test the vital signs, to start a new fluid bolus or continue a fluid bolus if one is being administered and to provide a maximum fluid bolus.

The administration signal is communicated by the intervention decision component 107 to the pump manager component 108. At stage 1122, the pump manager component 108 generates control signal(s) for infusion pump(s) such as the fluid pumps 108 based upon fluid administration signal to cause the fluid pumps 109 to take the appropriate action.

Figure 12:
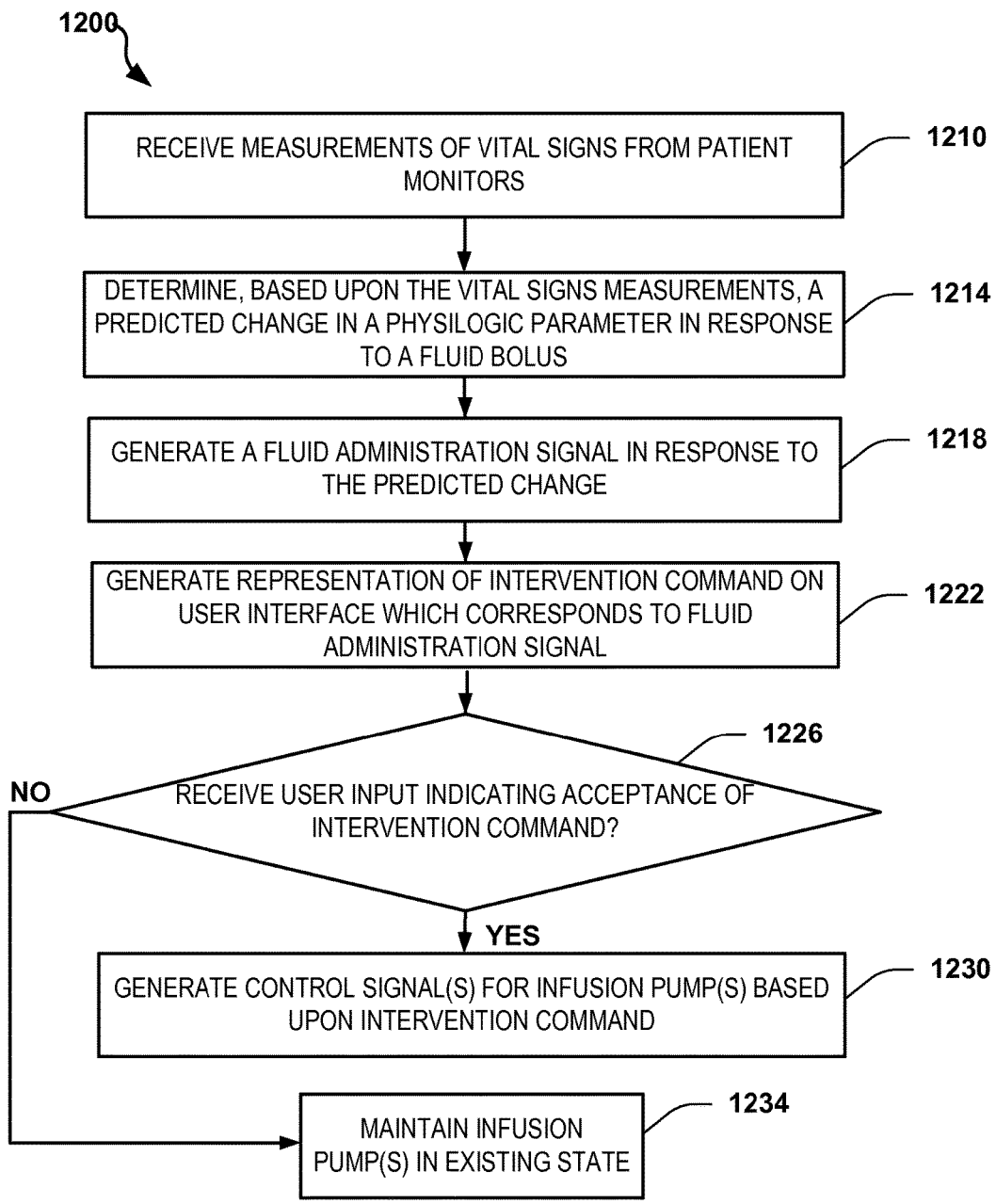
FIG. 12 is a flowchart depicting an exemplary method of providing patient-adaptive hemodynamic management including a user intervention in accordance with the disclosure.

Attention is now directed to FIG. 12 which is a flowchart depicting a exemplary method 1200 of providing patient-adaptive hemodynamic management including a user intervention in accordance with the disclosure. The process 1200 can be performed by the patient-adaptive hemodynamic management system 10 illustrated in FIGS. 1A and 1B including the control device 100 illustrated in FIGS. 2-8. The process 1200 is exemplary only and not limiting. The process 1200 can be altered, e.g., by having stages added, removed, rearranged, combined and/or performed concurrently.

At stage 1210, the vital signs manager 101 receives measurements of vital signs from clinical monitors 115 in a similar fashion as at stage 1110 discussed above. At stage 1214, the control device 100 determines, based upon the vital signs measurements, a predicted change in a physiologic parameter in response to a fluid bolus. Stage 1214 can be performed in a similar fashion to stage 1114 discussed above. At stage 1218, the intervention decision component 107 generates a fluid administration signal in response to the predicted change in a similar fashion as discussed above in reference to stage 1118.

At stage 1222, instead of generating a control signal with the pump manager component 107, as was done at stage 1122 in the process 1100, the intervention decision component 107 causes the user interface 810 to generate a representation of an intervention command on the user interface which corresponds to the fluid administration signal. At stage 1226, the user interface 810 receives a user input indicating acceptance or rejection of the intervention command. If the user input is a rejection, the process 1200 continues at stage 1234 where the current infusion or lack of infusion is continued in its existing state. If the user input received at stage 1226 is an acceptance, the process 1200 continues at stage 1230 where the user interface 810 or the intervention decision component 107 generates a control signal or signals based upon the intervention command received at stage 1226 and communicates the control signal(s) to the pump manager component 108.

Figure 13:
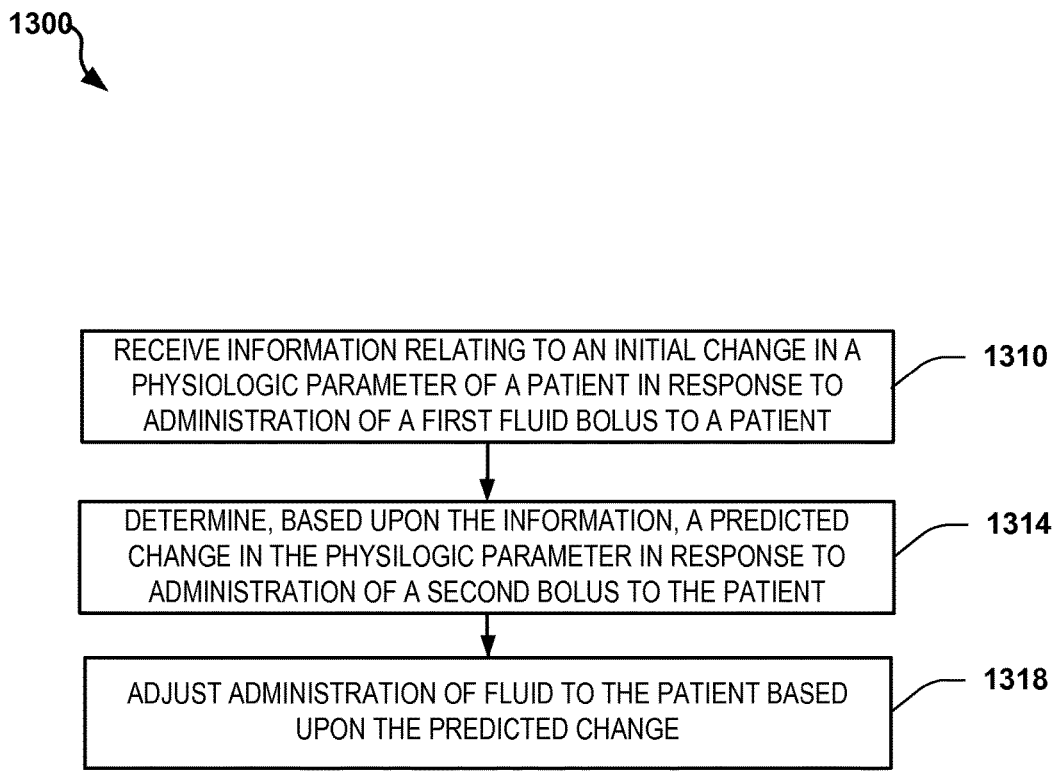
FIG. 13 is a flowchart depicting another exemplary method of providing patient-adaptive hemodynamic management in accordance with the disclosure.

Attention is now directed to FIG. 13 which is a flowchart depicting another exemplary process 1300 of providing patient-adaptive hemodynamic management in accordance with the disclosure. The process 1300 can be performed by the patient-adaptive hemodynamic management system 10 illustrated in FIGS. 1A and 1B including the control device 100 illustrated in FIGS. 2-8. The process 1300 is exemplary only and not limiting. The process 1300 can be altered, e.g., by having stages added, removed, rearranged, combined and/or performed concurrently.

The process 1300 starts at stage 1310 where the vitals manager component 101 receives information relating to an initial change in a physiologic parameter of a patient in response to administration of a first fluid bolus to the patient. At stage 1314, a predicted change in the physiologic parameter in response to administration of a second bolus to the patient is made by one or more of the population based predictor component 102, the log predictor component 104, the history analysis component 105 and the prediction engine 106 using any of the methods discussed above.

Upon determining the predicted change at stage 1314, the process 1300 continues to stage 1318 where the intervention decision component 107 and the pump manager component 108 adjust administration of the second fluid bolus to the patient based upon the predicted change.

Figure 14:
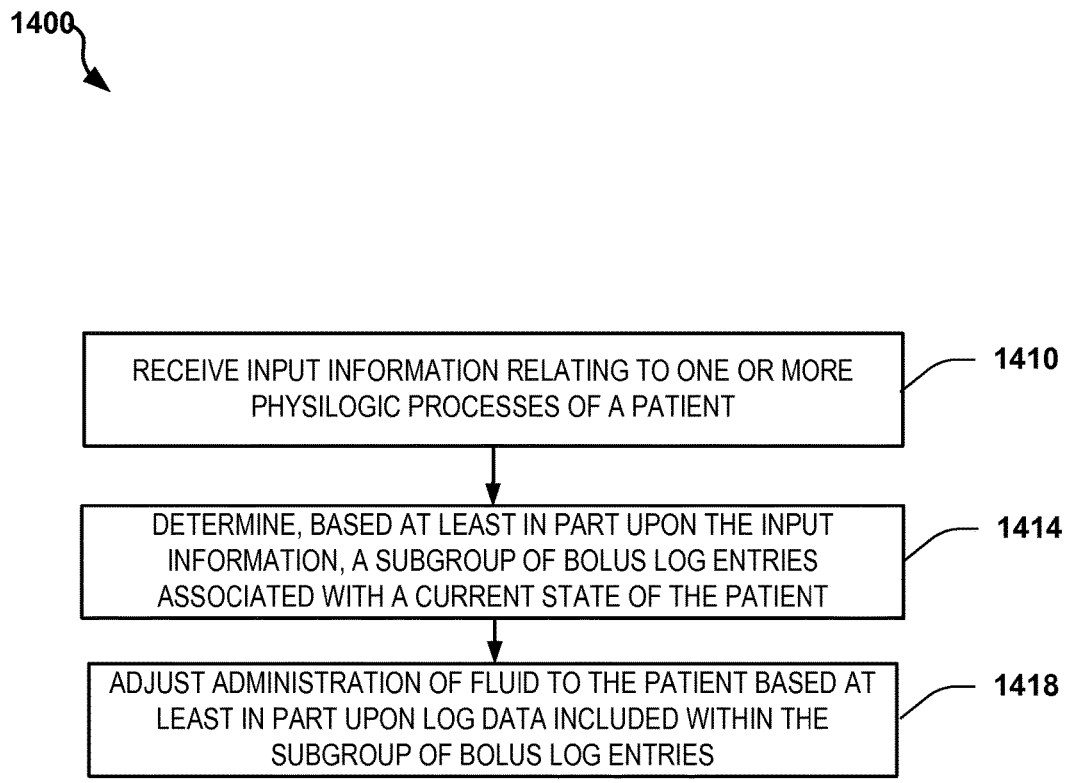
FIG. 14 is a flowchart depicting another exemplary method of providing patient-adaptive hemodynamic management in accordance with the disclosure.

Attention is now directed to FIG. 14 which is a flowchart depicting another exemplary process 1400 for providing patient-adaptive hemodynamic management in accordance with the disclosure. The process 1400 can be performed by the patient-adaptive hemodynamic management system 10 illustrated in FIGS. 1A and 1B including the control device 100 illustrated in FIGS. 2-8. The process 1400 is exemplary only and not limiting. The process 1400 can be altered, e.g., by having stages added, removed, rearranged, combined and/or performed concurrently.

At stage 1410, the vitals manager component 101 receives input information relating to one or more physiologic processes of a patient from one or more of the clinical monitors 115. At stage 1414, the fluid bolus log component 103 provides bolus log entries associated with a current state of the patient to the log predictor component 104 and the log predictor component 104 determines, based at least in part upon the input information, a subgroup of the bolus log entries. The subgroup of entries can be biased based on a state similarity analysis as discussed above in reference to FIG. 5.

At stage 1418, the intervention decision component 107 adjusts administration of fluid to the patient based at least in part upon log data included within the subgroup of bolus log entries.

Figure 15:
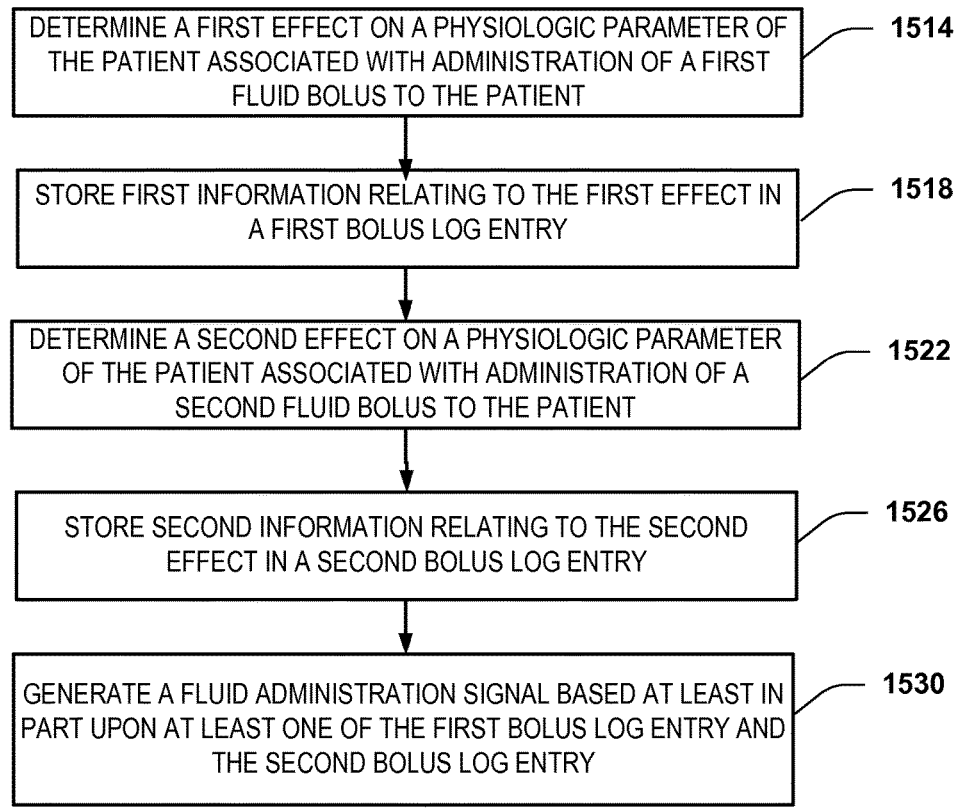
FIG. 15 is a flowchart depicting another exemplary method of providing patient-adaptive hemodynamic management in accordance with the disclosure.

Attention is now directed to FIG. 15 which is a flowchart depicting another exemplary process 1500 for providing patient-adaptive hemodynamic management in accordance with the disclosure. The process 1500 can be performed by the patient-adaptive hemodynamic management system 10 illustrated in FIGS. 1A and 1B including the control device 100 illustrated in FIGS. 2-8. The process 1500 is exemplary only and not limiting. The process 1500 can be altered, e.g., by having stages added, removed, rearranged, combined and/or performed concurrently.

The process 1500 starts at stage 1514 where the vitals manager component 101 determines a first effect on a physiologic parameter of the patient associated with administration of a first fluid bolus to the patient. The vitals manager component 101 or the fluid bolus log component 103 can determine the first effect by analyzing vitals signals received from the clinical monitors 115 and comparing the received signals to previously received and stored signals. The physiologic parameter can include one or more of cardiac output, stroke volume, etc.

At stage 1518, the fluid bolus log component 103 stores first information relating to the first effect in a first bolus log entry. The first bolus log entry can be the bolus log entry 400 discussed above in reference to FIG. 4. The first bolos log entry can be stored in memory such as RAM, ROM, flash or other type of computer readable storage medium.

At stage 1522, the vitals manager component 101 or the fluid bolus log component 103 determines a second effect on the physiologic parameter of the patient associated with administration of a second fluid bolus to the patient. The first effect can be determined by analyzing vitals signals received from the clinical monitors 115.

At stage 1526, the vitals manager component 101 or the fluid bolus log component 103 stores second information relating to the second effect in a second bolus log entry. The second bolus log entry can be a second bolus log entry 400 store in a computer readable storage medium.

At stage 1530, the intervention decision component 107 generates a fluid administration signal based at least in part upon at least one of the first bolus log entry and the second bolus log entry. The intervention decision component 107 can receive information indicating one or more of the type of fluid bolus to administer, an amount of fluid bolus to administer and or an rate and time over which to administer the fluid bolus from the log predictor component 104 or the prediction engine 106.

Figure 16:
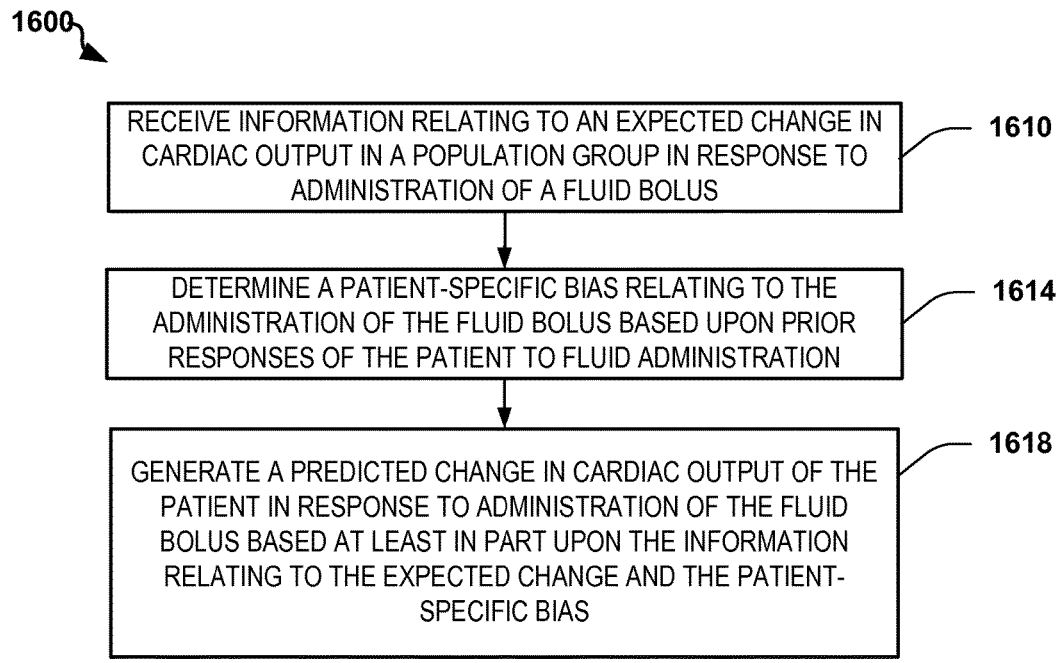
FIG. 16 is a flowchart depicting another exemplary method of providing patient-adaptive hemodynamic management in accordance with the disclosure.

Attention is now directed to FIG. 16 which is a flowchart depicting another exemplary process 1600 for providing patient-adaptive hemodynamic management in accordance with the disclosure. The process 1600 can be performed by the patient-adaptive hemodynamic management system 10 illustrated in FIGS. 1A and 1B including the control device 100 illustrated in FIGS. 2-8. The process 1600 is exemplary only and not limiting. The process 1600 can be altered, e.g., by having stages added, removed, rearranged, combined and/or performed concurrently.

The process 1600 starts at stage 1610 where the population based predictor component 102 receives information relating to an expected change in cardiac output in a population group in response to administration of a fluid bolus. The population based information can be stored in a computer readable medium such as one of the population reference tables 306 discussed above.

At stage 1614, the log predictor component 104 determines a patient-specific bias relating to the administration of the fluid bolus based upon prior responses of the patient to fluid administration. The bias can be accomplished by using a state similarity analysis of a subgroup of bolus log entries 502 as discussed above in reference to FIG. 5.

At stage 1618, the log predictor component 104 and/or the prediction engine 106 generates a predicted change in cardiac output of the patient in response to administration of the fluid bolus based at least in part upon the information relating to the expected change and the patient-specific bias.

Figure 17:
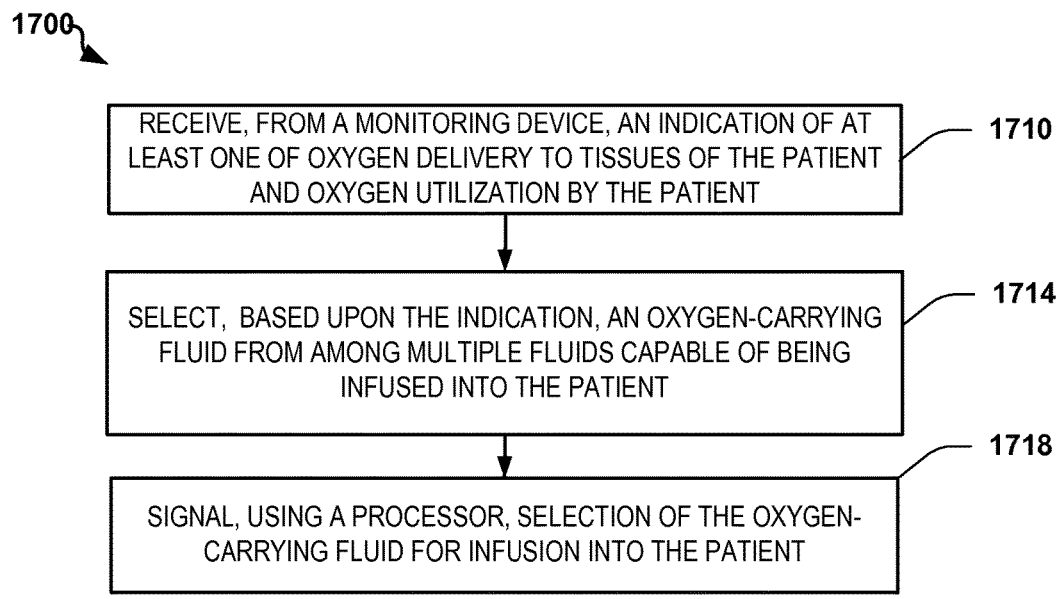
FIG. 17 is a flowchart depicting another exemplary method of providing patient-adaptive hemodynamic management in accordance with the disclosure.

Attention is now directed to FIG. 17 which is a flowchart depicting another exemplary process 1700 for providing patient-adaptive hemodynamic management in accordance with the disclosure. The process 1700 can be performed by the patient-adaptive hemodynamic management system 10 illustrated in FIGS. 1A and 1B including the control device 100 illustrated in FIGS. 2-8. The process 1700 is exemplary only and not limiting. The process 1700 can be altered, e.g., by having stages added, removed, rearranged, combined and/or performed concurrently.

At stage 1710, the vitals manager component 101 receives an indication of at least one of oxygen delivery to tissues of the patient and oxygen utilization by the patient. The indication can be received from a monitoring device such as one of the clinical monitors 115 or from an input to the user interface 810, for example. The vitals manager component 101 stores the indication in one of the bolus log entries in the vitals log table 202. The vitals log entry is then communicated to the intervention decision component 107. Alternatively, the intervention decision component 107 can receive the indication directly.

At stage 1714, based upon the indication, the intervention decision component 107 selects an oxygen-carrying fluid from among multiple fluids capable of being infused into the patient. At stage 1718, the intervention decision component 107 signals, using a processor, selection of the oxygen-carrying fluid for infusion into the patient.

Figure 18:
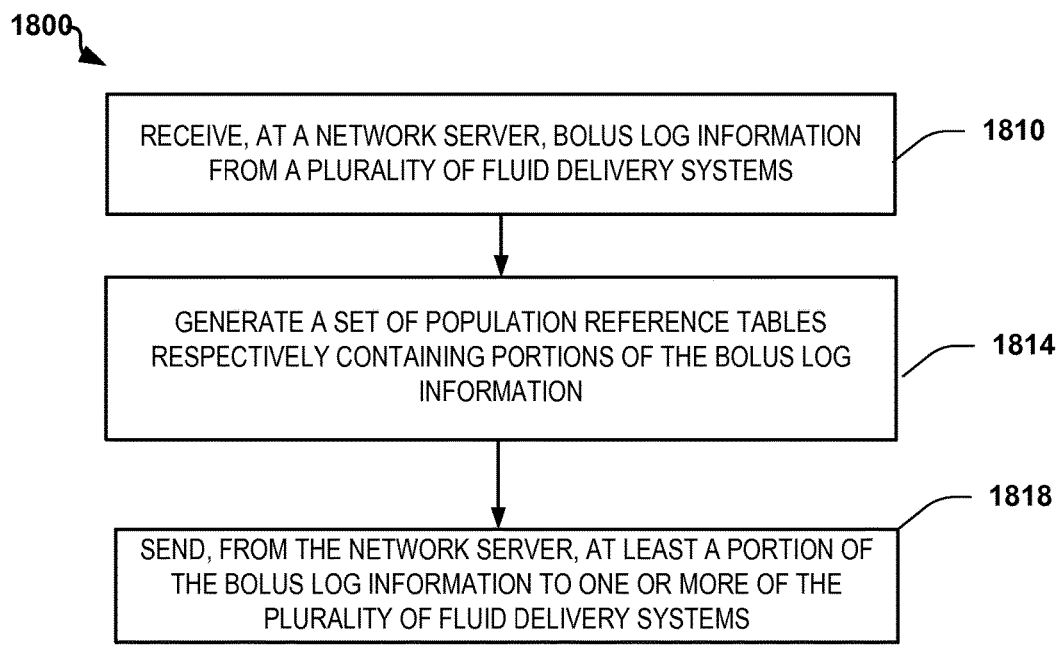
FIG. 18 is a flowchart depicting another exemplary method of providing patient-adaptive hemodynamic management in accordance with the disclosure.

Attention is now directed to FIG. 18 which is a flowchart depicting another exemplary process 1800 of providing patient-adaptive hemodynamic management in accordance with the disclosure. The process 1800 can be performed by the patient-adaptive hemodynamic management system 10 illustrated in FIGS. 1A and 1B including the control device 100 illustrated in FIGS. 2-8. The process 1800 is exemplary only and not limiting. The process 1800 can be altered, e.g., by having stages added, removed, rearranged, combined and/or performed concurrently.

At stage 1810, a network server receives bolus log information from a plurality of fluid delivery systems communicatively coupled to the network server. The fluid delivery systems can include, for example, the patient-adaptive hemodynamic management system 10 discussed above. After receiving the bolus log information, the process 1800 proceeds to stage 1814 where the network server generates a set of population reference tables respectively containing portions of the bolus log information such as, for example the population reference tables 306 discussed above in reference to FIG. 3.

At stage 1818, the network server sends at least a portion of the bolus log information to one or more of the plurality of fluid delivery systems such as the patient-adaptive hemodynamic management system 10. The patient-adaptive hemodynamic management system 10 can then utilize the population reference tables 306 to predict changes in physiologic parameters of a patient based on an ever increasing population of patients.

Figure 19:
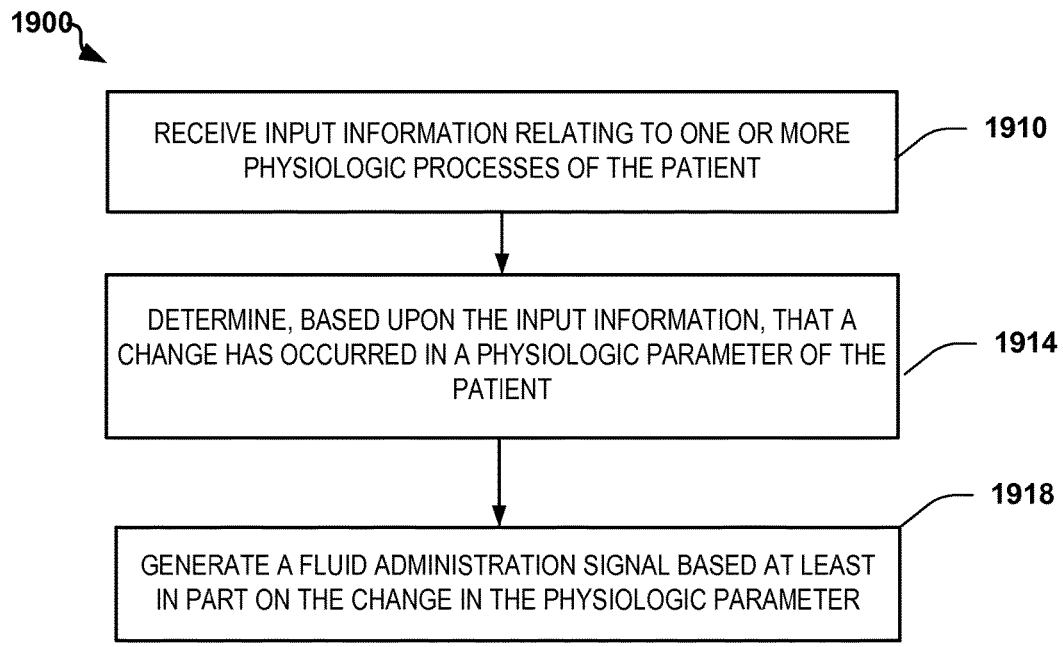
FIG. 19 is a flowchart depicting another exemplary method of providing patient-adaptive hemodynamic management in accordance with the disclosure.

Attention is now directed to FIG. 19 which is a flowchart depicting another exemplary process 1900 of providing patient-adaptive hemodynamic management in accordance with the disclosure. The process 1900 can be performed by the patient-adaptive hemodynamic management system 10 illustrated in FIGS. 1A and 1B including the control device 100 illustrated in FIGS. 2-8. The process 1900 is exemplary only and not limiting. The process 1900 can be altered, e.g., by having stages added, removed, rearranged, combined and/or performed concurrently.

At stage 1910, the vitals manager component 101 receive input information relating to one or more physiologic processes of the patient. The input information can be received from one of the clinical monitors 115 and/or from the user interface 810, for example. The vitals manager component 101 stores information indicative of the input information in a bolus log entry of the bolus log table 202.

At stage 1914, the intervention decision component 107 determines, based upon the input information obtained by receiving the bolus log entry containing the stored information, that a change has occurred in a physiologic parameter of the patient. In response, depending on the physiologic parameter being in one of a plurality of range of values such as one of the ranges 701, 702, 703 or 704 discussed above in reference to FIG. 7, the intervention decision component 107 generates a fluid administration signal based at least in part on the change in the physiologic parameter. As discussed above, the administration signal can stop a current bolus, start a new bolus, increase or decrease an infusion rate or maximize an infusion rate, depending on which of the plurality of threshold ranges the physiologic parameter is in.

Figure 20:
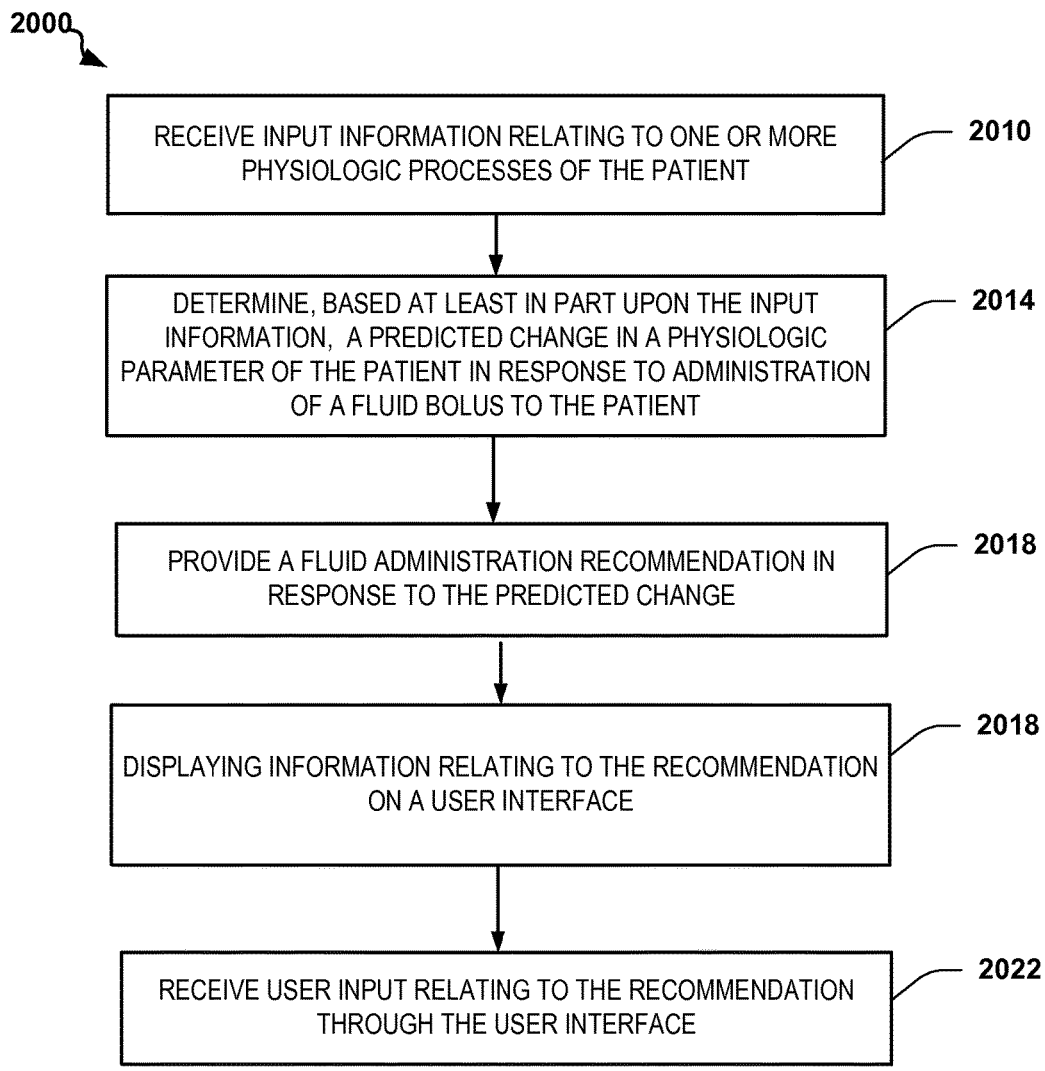
FIG. 20 is a flowchart depicting another exemplary method of providing patient-adaptive hemodynamic management in accordance with the disclosure.

Attention is now directed to FIG. 20 which is a flowchart depicting another exemplary process 2000 for providing patient-adaptive hemodynamic management in accordance with the disclosure. The process 2000 can be performed by the patient-adaptive hemodynamic management system 10 illustrated in FIGS. 1A and 1B including the control device 100 illustrated in FIGS. 2-8. The process 2000 is exemplary only and not limiting. The process 2000 can be altered, e.g., by having stages added, removed, rearranged, combined and/or performed concurrently.

At stage 2010, the vitals manager component 101 receives input information relating to one or more physiologic processes of the patient 110. The input information can be received from one of the clinical monitors 115 or from the user interface 810, for example. Upon receiving the input information, the vitals manager component 101 stores information indicative of the input information in a bolus log entry of the bolus log table 202.

At stage 2014, one or more of the population based predictor component 102, the log predictor component 104, the history analysis component 105 and the prediction engine 106 determines, based at least in part upon the input information using the methods discussed above, a predicted change in a physiologic parameter of the patient 110 in response to administration of a fluid bolus to the patient.

At stage 2018, one or more of the components of the control device 100, e.g., the intervention decision component 107 or the prediction engine 106, provides a fluid administration recommendation in response to the predicted change to the user interface 810. At stage 2022, a display of the user interface 810 displays information relating to the recommendation on the user interface 810. At stage 2022, the intervention decision component 107 or the user interface 810 receives user input relating to the recommendation through the user interface 810. The intervention decision component 107 or the user interface 810 can then generate an administration signal to the pump manager component 108 related to the recommendation.

Figure 21:
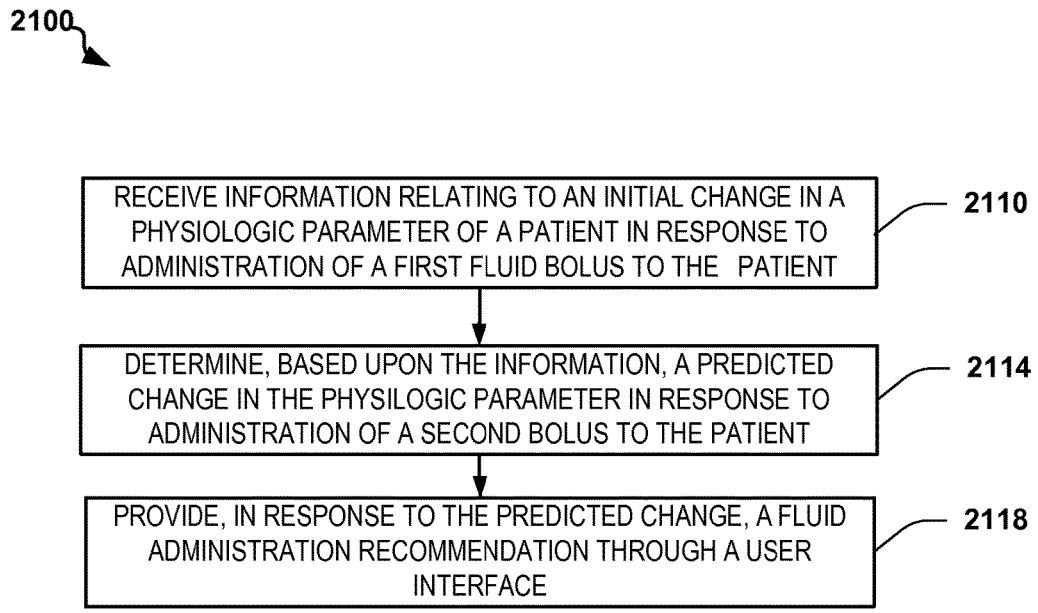
FIG. 21 is a flowchart depicting another exemplary method of providing patient-adaptive hemodynamic management in accordance with the disclosure.

Attention is now directed to FIG. 21 which is a flowchart depicting another exemplary process 2100 for providing patient-adaptive hemodynamic management in accordance with the disclosure. The process 2100 can be performed by the patient-adaptive hemodynamic management system 10 illustrated in FIGS. 1A and 1B including the control device 100 illustrated in FIGS. 2-8. The process 2100 is exemplary only and not limiting. The process 2100 can be altered, e.g., by having stages added, removed, rearranged, combined and/or performed concurrently.

At stage 2110, the vitals manager component 101 receives information relating to an initial change in a physiologic parameter of a patient 110 in response to administration of a first fluid bolus to the patient 110. The received information can be received from one of the clinical monitors 115 or from the user interface 810, for example. Upon receiving the input information, the vitals manager component 101 stores information indicative of the input information in a bolus log entry of the bolus log table 202.

At stage 2114, one or more of the population based predictor component 102, the log predictor component 104, the history analysis component 105 or the prediction engine 106 determines, based upon the information, a predicted change in the physiologic parameter in response to administration of a second bolus to the patient.

At stage 2118, the prediction engine 106 or the intervention decision engine 107 can provide a fluid administration recommendation through the user interface 810 in response to the predicted change.

Figure 22:
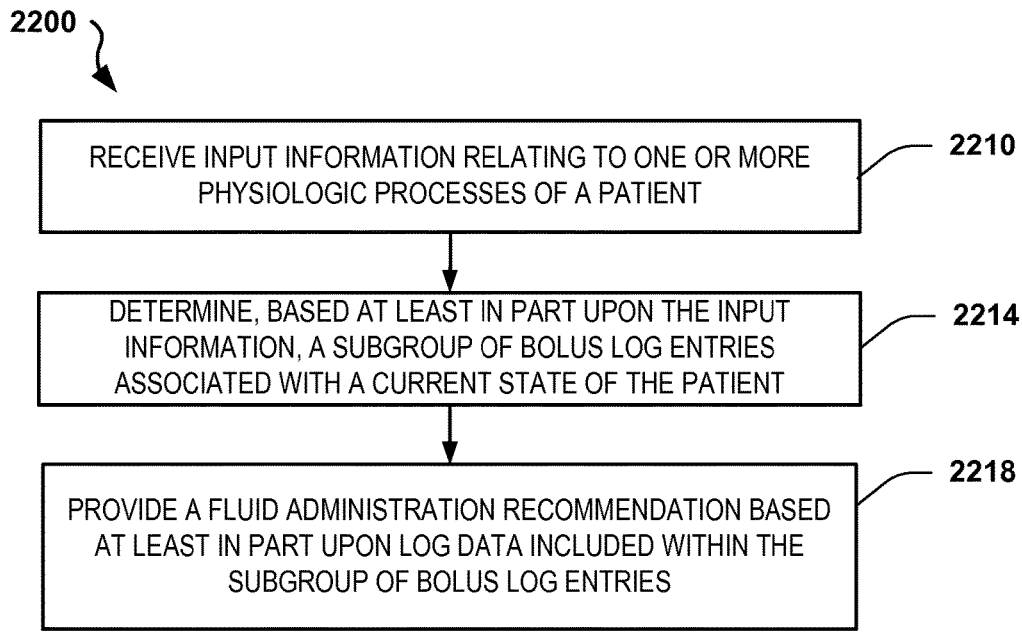
FIG. 22 is a flowchart depicting another exemplary method of providing patient-adaptive hemodynamic management in accordance with the disclosure.

Attention is now directed to FIG. 22 which is a flowchart depicting another exemplary process 2200 for providing patient-adaptive hemodynamic management in accordance with the disclosure. The process 2200 can be performed by the patient-adaptive hemodynamic management system 10 illustrated in FIGS. 1A and 1B including the control device 100 illustrated in FIGS. 2-8. The process 2200 is exemplary only and not limiting. The process 2200 can be altered, e.g., by having stages added, removed, rearranged, combined and/or performed concurrently.

At stage 2210, the vitals manager component 101 receives input information relating to one or more physiologic processes of a patient. The input information can be received from one of the clinical monitors 115 or from the user interface 810, for example. Upon receiving the input information, the vitals manager component 101 stores information indicative of the input information in a bolus log entry of the bolus log table 202.

At stage 2210, one or more of the log predictor component 104, the history analysis component 105 or the prediction engine 106 determines, based at least in part upon the input information, a subgroup of bolus log entries associated with a current state of the patient.

At stage 2214, the prediction engine 106 or the intervention decision engine 107 can provide a fluid administration recommendation based at least in part upon log data included within the subgroup of bolus log entries. The fluid administration recommendation can be provided to the user interface 810 to prompt a user for acceptance or rejection of the recommendation. Alternatively, the fluid administration recommendation can be converted to a signal to cause the fluid pump manager component 108 to administer the recommendation automatically.

Figure 23:
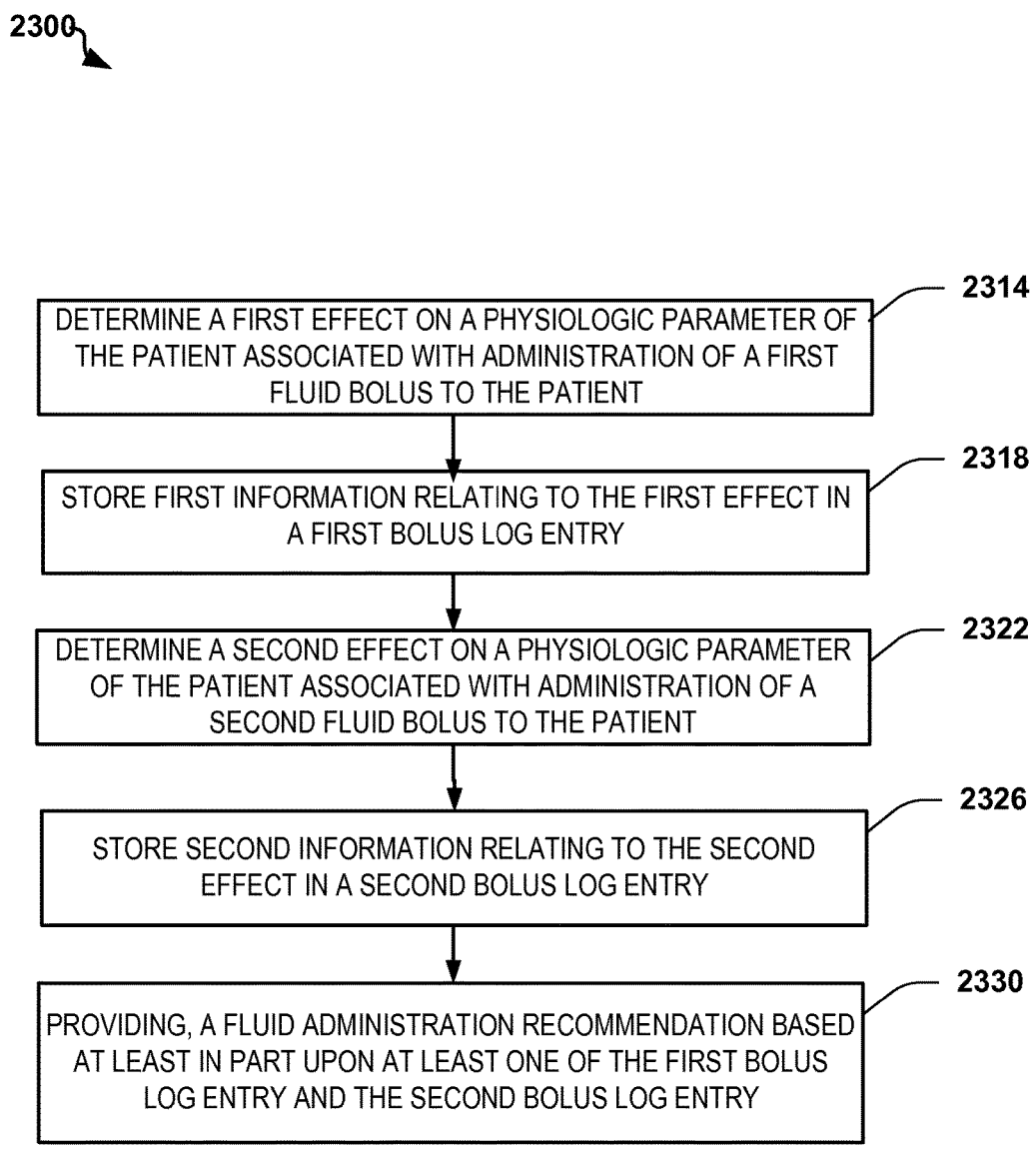
FIG. 23 is a flowchart depicting yet another exemplary method of providing patient-adaptive hemodynamic management in accordance with the disclosure.

Attention is now directed to FIG. 23 which is a flowchart depicting yet another exemplary process 2300 for providing patient-adaptive hemodynamic management in accordance with the disclosure. The process 2300 can be performed by the patient-adaptive hemodynamic management system 10 illustrated in FIGS. 1A and 1B including the control device 100 illustrated in FIGS. 2-8. The process 2300 is exemplary only and not limiting. The process 2300 can be altered, e.g., by having stages added, removed, rearranged, combined and/or performed concurrently.

At stage 2314, the vitals manager component 101 or the fluid bolus log component 103 determines a first effect on a physiologic parameter of the patient associated with administration of a first fluid bolus to the patient.

At stage 2318, the fluid bolus log component 103 stores first information relating to the first effect in a first bolus log entry 400. At stage 2322, the vitals manager component 101 or the fluid bolus log component 103 determines a second effect on a physiologic parameter of the patient associated with administration of a second fluid bolus to the patient.

At stage 2326, the fluid bolus log component 103 stores second information relating to the second effect in a second bolus log entry 400.

At stage 2330, one or more of the population based predictor component 102, the log predictor component 104, the history analysis component 105, the intervention decision engine 107 or the prediction engine 106 provides, a fluid administration recommendation based at least in part upon at least one of the first bolus log entry and the second bolus log entry using the methods discussed above. The recommendation can be provided to the user interface 810 to prompt a user for acceptance or rejection of the recommendation. Alternatively, the fluid administration recommendation can be converted to a signal to cause the fluid pump manager component 108 to administer the recommendation automatically.

Figure 24:
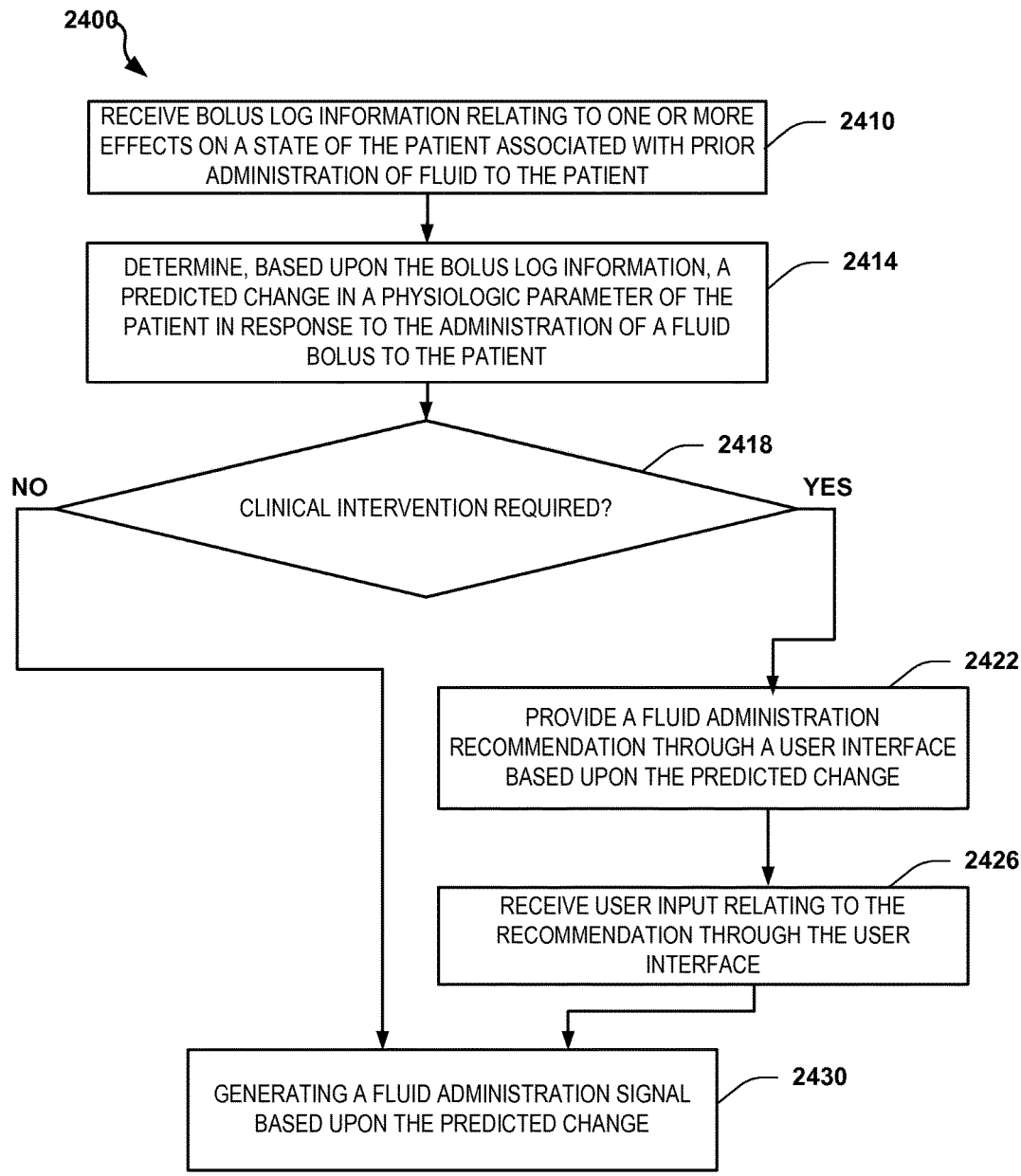
FIG. 24 is a flowchart depicting another exemplary method of providing patient-adaptive hemodynamic management including a clinical intervention in accordance with the disclosure.

Attention is now directed to FIG. 24 which is a flowchart depicting another exemplary process 2400 for providing patient-adaptive hemodynamic management including a clinical intervention in accordance with the disclosure. The process 2400 can be performed by the patient-adaptive hemodynamic management system 10 illustrated in FIGS. 1A and 1B including the control device 100 illustrated in FIGS. 2-8. The process 2400 is exemplary only and not limiting. The process 2400 can be altered, e.g., by having stages added, removed, rearranged, combined and/or performed concurrently.

At stage 2410, the log predictor component 104 receives bolus log information, e.g., from the fluid bolus log component 103, relating to one or more effects on a state of the patient associated with prior administration of fluid to the patient. At stage 2414, the log predictor component 104 determines, based upon the bolus log information, a predicted change in a physiologic parameter of the patient in response to the administration of a fluid bolus to the patient.

At decision block 2418, the intervention decision component 107 determines if clinical intervention is required. The decision can be made based on the physiologic parameter lies in one of a plurality of range of values such as the one of the ranges 701, 702, 703 or 704 discussed above in reference to FIG. 7. If it is determined that clinical intervention is not required, the process 2400 continues to stage 2430 where the intervention decision component 107 and the pump manager component 108 communicate with each other to generate a fluid administration signal based upon the predicted change.

If, at stage 2418, it is determined that clinical intervention is required, the process 2400 continues at stage 2422 where the intervention decision component 107 provides a fluid administration recommendation through the user interface 810 based upon the predicted change. The fluid administration signal can recommend to a user what fluid administration is recommended.

At stage 2426, the intervention decision component 107 or the user interface 810 receives user input relating to the recommendation through the user interface 810. After receiving the user input, the process continues at stage 2430 where the intervention decision component 107 or the user interface 810 generates a fluid administration signal to the pump manager component 108 to affect the fluid administration to the patient based upon the predicted change and further based upon the user input.

Figure 25:
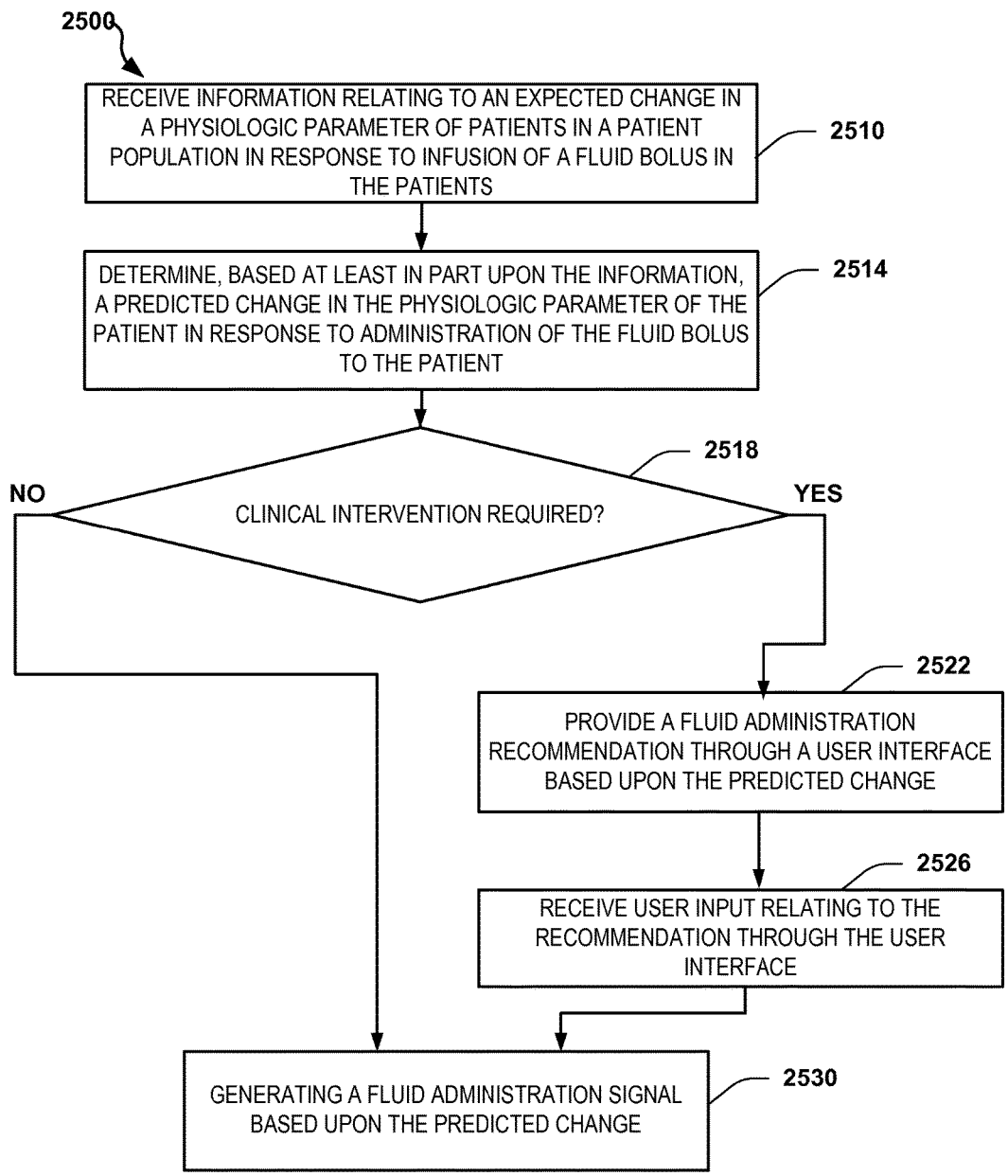
FIG. 25 is a flowchart depicting another exemplary method of providing patient-adaptive hemodynamic management including a clinical intervention in accordance with the disclosure.

Attention is now directed to FIG. 25 which is a flowchart depicting another exemplary process 2500 of providing patient-adaptive hemodynamic management including a clinical intervention in accordance with the disclosure. The process 2500 can be performed by the patient-adaptive hemodynamic management system 10 illustrated in FIGS. 1A and 1B including the control device 100 illustrated in FIGS. 2-8. The process 2500 is exemplary only and not limiting. The process 2500 can be altered, e.g., by having stages added, removed, rearranged, combined and/or performed concurrently.

At stage 2510, the population based predictor component 102 receives information relating to an expected change in a physiologic parameter of patients in a patient population in response to infusion of a fluid bolus in the patients. At stage 2414, the population based predictor component 102 determines, based at least in part upon the information using the methods discussed above, a predicted change in the physiologic parameter of the patient in response to administration of the fluid bolus to the patient.

At decision block 2518, the intervention decision component 107 determines if clinical intervention is required. The decision can be made based on the physiologic parameter lies in one of a plurality of range of values such as the one of the ranges 701, 702, 703 or 704 discussed above in reference to FIG. 7. If it is determined that clinical intervention is not required, the process 2500 continues to stage 2530 where the intervention decision component 107 and the pump manager component 108 communicate with each other to generate a fluid administration signal based upon the predicted change.

If, at stage 2518, it is determined that clinical intervention is required, the process 2500 continues at stage 2522 where the intervention decision component 107 provides a fluid administration recommendation through the user interface 810 based upon the predicted change. The fluid administration signal can recommend to a user what fluid administration is recommended.

At stage 2526, the intervention decision component 107 or the user interface 810 receives user input relating to the recommendation through the user interface 810. After receiving the user input, the process continues at stage 2530 where the intervention decision component 107 or the user interface 810 generates a fluid administration signal to the pump manager component 108 to affect the fluid administration to the patient based upon the predicted change and further based upon the user input.

Figure 26:
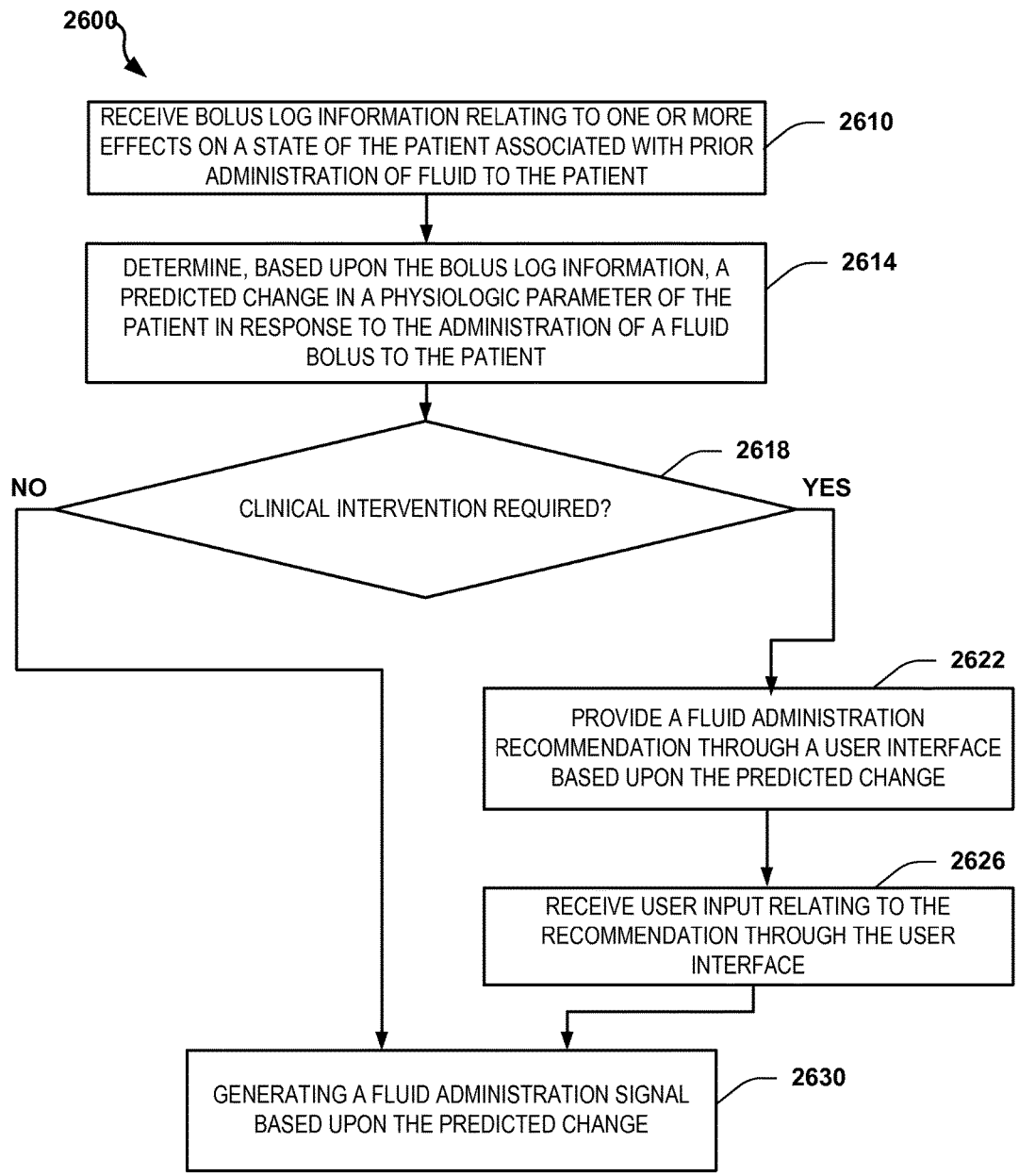
FIG. 26 is a flowchart depicting yet another exemplary method of providing patient-adaptive hemodynamic management including a clinical intervention in accordance with the disclosure.

Attention is now directed to FIG. 26 which is a flowchart depicting yet another exemplary process 2600 of providing patient-adaptive hemodynamic management including a clinical intervention in accordance with the disclosure. The process 2600 can be performed by the patient-adaptive hemodynamic management system 10 illustrated in FIGS. 1A and 1B including the control device 100 illustrated in FIGS. 2-8. The process 2600 is exemplary only and not limiting. The process 2600 can be altered, e.g., by having stages added, removed, rearranged, combined and/or performed concurrently.

At stage 2610, the fluid bolus log component 103 receives bolus log information relating to one or more effects on a state of the patient associated with prior administration of fluid to the patient. At stage 2614, the log predictor component 104 determines, based upon the bolus log information and using the methods discussed above, a predicted change in a physiologic parameter of the patient in response to the administration of a fluid bolus to the patient.

At decision block 2618, the intervention decision component 107 determines if clinical intervention is required. The decision can be made based on the physiologic parameter lies in one of a plurality of range of values such as the one of the ranges 701, 702, 703 or 704 discussed above in reference to FIG. 7. If it is determined that clinical intervention is not required, the process 2600 continues to stage 2630 where the intervention decision component 107 and the pump manager component 108 communicate with each other to generate a fluid administration signal based upon the predicted change.

If, at stage 2618, it is determined that clinical intervention is required, the process 2600 continues at stage 2622 where the intervention decision component 107 provides a fluid administration recommendation through the user interface 810 based upon the predicted change. The fluid administration signal can recommend to a user what fluid administration is recommended.

At stage 2626, the intervention decision component 107 or the user interface 810 receives user input relating to the recommendation through the user interface 810. After receiving the user input, the process continues at stage 2630 where the intervention decision component 107 or the user interface 810 generates a fluid administration signal to the pump manager component 108 to affect the fluid administration to the patient based upon the predicted change and further based upon the user input.

A display of a possible user interface could comprise a standard "Starling Curve" of ventricular function, a graphical indicator of where the patient is perceived to be presently along that curve, and a band showing the ideal range of the curve for the patient. In addition, minimum and maximum curves can be displayed showing the observed ranges of cardiac function in a given patient (not shown).

FIG. 27 is a summary of a table of results from initial studies using the methodology of the control device 100 in simulations. The performance of the control device 100 was compared to the performance of anesthesiologists across a number of dimensions. The table in FIG. 27 is presented as evidence of the effectiveness of the methodology of the control device 100 in the studies. Closed-loop management of fluid resuscitation has historically been difficult. The table in FIG. 27 is representative of simulation data for a closed-loop fluid-management algorithm using pulse pressure variation (PPV) as the input variable.

Using a simulator which includes physiologic PPV output, twenty practicing anesthesiology residents and faculty were asked to manage fluids and pressors for a one-hour simulated hemorrhage case of 2 L blood loss over 20 minutes (group 1). One week later, they repeated the simulation, but this time fluids were secretly managed by the closed-loop system while practitioner fluid administrations were ignored and only the pressors were entered (group 2). The simulation was also run twenty times with only the closed-loop (group 3) and twenty times with no management (group 4). As illustrated by the data included in FIG. 27, conditions across all groups were similar at baseline for simulated patient weight, height, heart rate (HR), mean arterial pressure (MAP), and cardiac output (CO). Once the hemorrhage began, the closed loop groups (2&3) intervened significantly earlier than the practitioners (group 1) and gave more fluid. The mean and final CO was higher in both closed-loop groups than in the practitioners group, and the coefficient of variance was lower. There was no difference in MAP between intervention groups, but all were significantly higher than the unmanaged group. In conclusion, the data demonstrate that closed-loop management of fluid resuscitation is feasible using a dynamic parameter based algorithm and that this approach can be used to optimize cardiac output.

In one or more exemplary embodiments, the functions, methods and processes described may be implemented in hardware, software, firmware, or any combination thereof. If implemented in software, the functions may be stored on or encoded as one or more instructions or code on a computer-readable medium. Computer-readable media includes computer storage media. Storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

As used herein, computer program products comprising computer-readable media including all forms of computer-readable medium except, to the extent that such media is deemed to be non-statutory, transitory propagating signals.

It is understood that the specific order or hierarchy of steps or stages in the processes and methods disclosed are examples of exemplary approaches. Based upon design preferences, it is understood that the specific order or hierarchy of steps in the processes may be rearranged while remaining within the scope of the present disclosure. The accompanying method claims present elements of the various steps in a sample order, and are not meant to be limited to the specific order or hierarchy presented.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps or stages of a method, process or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

The previous description of the disclosed embodiments is provided to enable any person skilled in the art to make or use the present disclosure. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

The disclosure is not intended to be limited to the aspects shown herein, but is to be accorded the full scope consistent with the specification and drawings, wherein reference to an element in the singular is not intended to mean "one and only one" unless specifically so stated, but rather "one or more." Unless specifically stated otherwise, the term "some" refers to one or more. A phrase referring to "at least one of" a list of items refers to any combination of those items, including single members. As an example, "at least one of: a, b, or c" is intended to cover: a; b; c; a and b; a and c; b and c; and a, b and c.

The previous description of the disclosed aspects is provided to enable any person skilled in the art to make or use the present disclosure. Various modifications to these aspects will be readily apparent to those skilled in the art, and the generic principles defined herein may be applied to other aspects without departing from the spirit or scope of the disclosure. Thus, the disclosure is not intended to be limited to the aspects shown herein but is to be accorded the widest scope consistent with the principles and novel features disclosed herein. It is intended that the following claims and their equivalents define the scope of the disclosure.

What is claimed is:

1. A computer-implemented method for providing clinical decision support relating to the administration of proposed fluid to a patient, the method comprising:
   intravenously administering one or more fluid boluses to the patient, each of which lacks vasoactive or inotropic medication and, during or after administering the fluid, receiving input information comprising data representing one or more physiologic processes of a patient resulting from response to the administration of the intravenous fluid, and storing said information as one or more bolus log entries;
   determining, based at least in part upon the input information, a subgroup of bolus log entries associated with a current state of the patient, the subgroup containing said data;

using a processor to generate a fluid administration signal for intravenously administering a treating fluid for the purpose of intravascular volume expansion, wherein the treating fluid lacks vasoactive or inotropic medication and the signal is based at least in part upon log data included within the subgroup of bolus log entries; and administering the proposed fluid to the patient.

2. The method of claim 1 in which the fluid boluses are each saline solution.

3. The method of claim 1 in which intravenously administering said one or more boluses to the patient comprises:

providing a first fluid pump coupled to at least one fluid source;

coupling the first fluid pump to the patient to administer a fluid to the patient to provide said input information.

4. The method of claim 3 in which administering a fluid for the purpose of intravascular volume expansion comprises providing a second fluid pump coupled to said treating fluid; and coupling the second fluid pump to the patient to administer the treating fluid to the patient.

5. The method of claim 4 comprising providing a display coupled to the first and second fluid pumps.

* * * * *